United States Patent
Wan et al.

(10) Patent No.: US 11,912,770 B2
(45) Date of Patent: Feb. 27, 2024

(54) BLOCKING TYPE PD-L1 SINGLE-DOMAIN CAMEL ANTIBODY AND APPLICATION THEREOF

(71) Applicant: SHANGHAI NOVAMAB BIOPHARMACEUTICALS CO., LTD., Shanghai (CN)

(72) Inventors: Yakun Wan, Shanghai (CN); Min Zhu, Shanghai (CN); Xiaoning Shen, Shanghai (CN); Junwei Gai, Shanghai (CN)

(73) Assignee: SHANGHAI NOVAMAB BIOPHARMACEUTICALS CO., LTD., Shanghai (CN)

( * ) Notice: Subject to any disclaimer, the term of this patent is extended or adjusted under 35 U.S.C. 154(b) by 678 days.

(21) Appl. No.: 16/970,083

(22) PCT Filed: Feb. 14, 2019

(86) PCT No.: PCT/CN2019/075112
§ 371 (c)(1),
(2) Date: Jan. 12, 2021

(87) PCT Pub. No.: WO2019/158113
PCT Pub. Date: Aug. 22, 2019

(65) Prior Publication Data
US 2021/0261667 A1     Aug. 26, 2021

(30) Foreign Application Priority Data
Feb. 14, 2018 (CN) .......................... 201810151835.5

(51) Int. Cl.
*C07K 16/28* (2006.01)
*A61K 39/00* (2006.01)

(52) U.S. Cl.
CPC .... *C07K 16/2827* (2013.01); *A61K 2039/505* (2013.01); *C07K 2317/24* (2013.01); *C07K 2317/35* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01)

(58) Field of Classification Search
CPC .......... A61K 2039/505; C07K 2317/24; C07K 2317/35; C07K 2317/565; C07K 2317/567; C07K 2317/569; C07K 2317/76; C07K 2317/92; C07K 2317/94
See application file for complete search history.

(56) References Cited

FOREIGN PATENT DOCUMENTS

| CN | 1234073 A | 11/1999 | | |
|---|---|---|---|---|
| CN | 106397592 A | 2/2017 | | |
| CN | 106939047 A | 7/2017 | | |
| WO | 2017194782 A2 | 11/2017 | | |
| WO | WO-2017194782 A2 * | 11/2017 | .......... | A61K 31/704 |

* cited by examiner

*Primary Examiner* — Aurora M Fontainhas
*Assistant Examiner* — Selam Berhane
(74) *Attorney, Agent, or Firm* — NKL Law; Allen Xue

(57) ABSTRACT

Provided are a single-domain antibody against human programmed death-ligand 1 (PD-L1) and application thereof. The PD-L1 binding molecule of the present invention can be used for treating and/or preventing, or diagnosing PD-L1 related diseases such as tumors.

15 Claims, 12 Drawing Sheets
Specification includes a Sequence Listing.

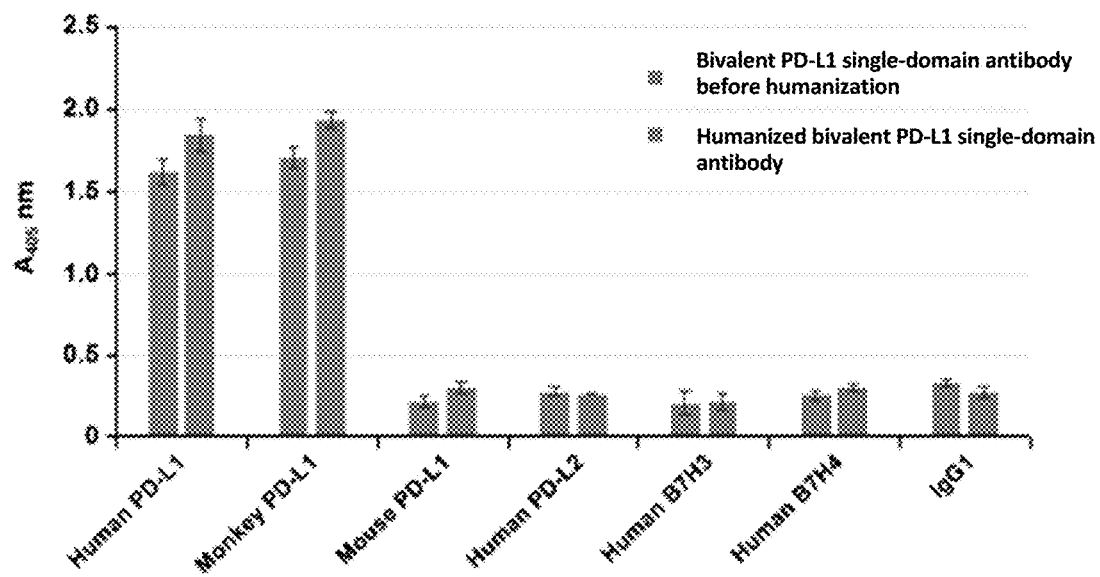
FIG. 10
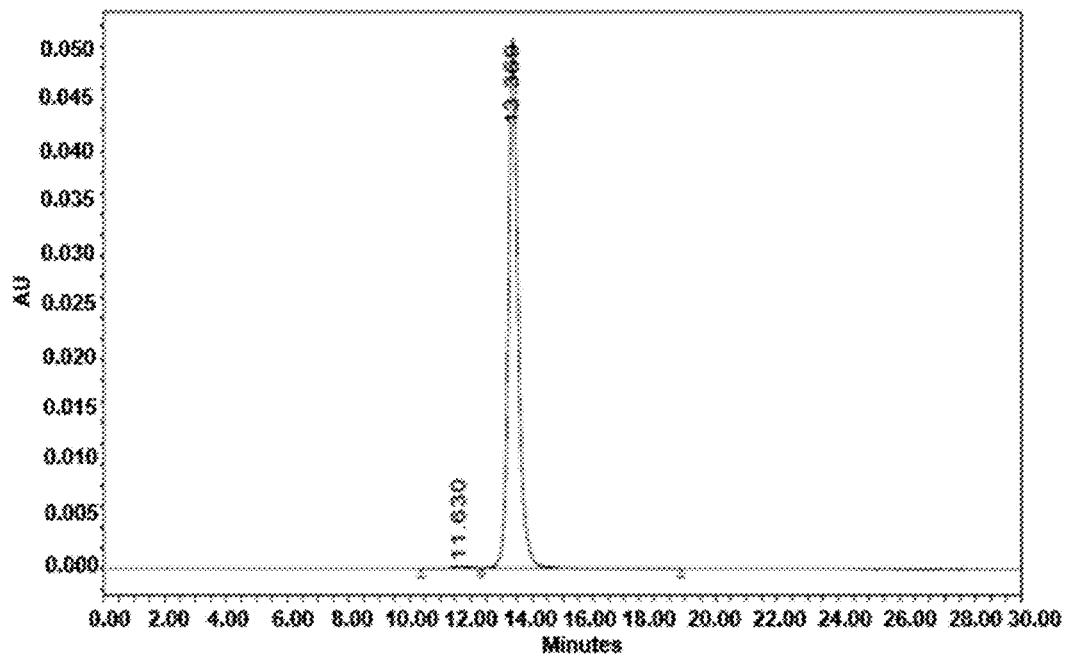

| | Component Results | | | |
|---|---|---|---|---|
| | Monomer_RT | Monomer_PeakArea | Aggregate_PeakArea | Fragment_PeakArea |
| 1 | 13.369 | 99.07 | 0.93 | 0.00 |

FIG. 11

BLOCKING TYPE PD-L1 SINGLE-DOMAIN CAMEL ANTIBODY AND APPLICATION THEREOF

INCORPORATION OF SEQUENCE LISTING

This application contains a sequence listing in Computer Readable Form (CRF). The CFR file containing the sequence listing entitled "PB4084096-seq.txt", which was created on Dec. 29, 2020 and filed on Aug. 14, 2020, and is 103,170.645 bytes in size. The information in the sequence listing is incorporated herein by reference in entirety.

TECHNICAL FIELD

The present invention relates to the technical field of biomedicine or bio-pharmaceuticals, and more particularly relates to a blocking type PD-L1 single-domain camel antibody and application thereof.

BACKGROUND

Tumor immune escape is caused by the tumor cells which escape the collective immune recognition and attack by alternation of tumor cells themselves or the microenvironment. Because tumor immunotherapy has advantages such as less damage, effective inhibition of tumor growth and metastasis, it has become an urgent need for clinical treatment of tumor. Programmed death 1/programmed death ligand 1 (PD-1/PD-L1), as a pair of negative immune costimulatory molecules, participate in tumor immune escape. PD-1/PD-L1 are new members of B7/CD28 costimulatory molecule superfamily, can mediate negative costimulatory signals, can effectively inhibit function and proliferation of T cells and B cells, and reduce secretion of IL-2, IL-10 and IFN-γ cytokines. The immune regulation involved in this inhibitory pathway is of great significance in the research of tumor immunity, transplantation immunity, viral infection, autoimmunity and some other diseases.

Programmed death ligand 1 (or PD-L1), also known as CD274, is a member of the B7 family. PD-L1 is a type I transmembrane protein with a molecular weight of about 30-35 KD. The receptor PD-1 thereof is one of the members of immunoglobulin B7-CD28 family, consists of an extracellular region, a hydrophobic transmembrane region, and an intracellular region wherein the intracellular region contains an immunoreceptor tyrosine-based inhibitory motif (ITIM), and an immunoreceptor tyrosine-based switch motif (ITSM). Among them, the activation of ITSM is closely related to the response activity of effector T cells. PD-1 can be expressed in activated $CD4^+$ T cells, $CD8^+$ T cells, B cells, natural killer T cells, monocytes and dendritic cells. Additionally, PD-1 is also expressed in regulatory T cells (Treg) and can promote the proliferation of Treg cells and suppress immune response. The human PD-L1 molecule can be constitutively expressed in non-lymphoid tissues such as placenta, heart, liver, lung, kidney, skeletal muscle, and some hematopoietic cells, and is also moderately expressed in lymphatic tissues such as thymus, lymph nodes, and spleen. Moreover, PD-L1 is also expressed in cancer cells such as lung cancer, liver cancer, breast cancer, and ovarian cancer cells, and the expression can also be up-regulated in the cancer tissue after induction. In a healthy body, the activation of PD-1/PD-L1 signaling pathway can minimize the damage of surrounding tissues caused by immune response and avoid the occurrence of autoimmune diseases. However, the activation of PD-1/PD-L1 signaling pathway changes the local microenvironment of tumor so as to reduce immunology effect of T cells, thereby mediating tumor immune escape and promoting tumor growth. The expression of PD-L1 on tumors is associated with a decrease of survival rate for esophageal cancer, pancreatic cancer and other types of cancer, highlighting that this pathway can be used as a new promising tumor immunotherapy target as confirmed by many experiments.

Single-domain antibody, as a novel small molecule antibody fragment, is obtained from the heavy chain variable region (VHH) clones of camel natural heavy chain antibody. The molecular weight of a single-domain antibody is only 12-15 KD, which is one-tenth of a conventional monoclonal antibody, and the size is only 2-4 nM. Single-domain antibody has excellent biological properties. It not only has complete antigen binding sites, but also overcomes the shortcomings of natural antibody having large molecular weight, for example, having good tissue penetration, high specificity and good water solubility. Because of its special structural properties, it has both advantages of traditional antibody and small molecule drug, and essentially avoids the shortcomings of traditional antibody such as long development cycle, low stability, and harsh storage conditions, so that it shows a wide and potential application in immunological diagnosis and treatment. There is still an urgent need in the art for developing an antibody, especially anti-PD-L1 single-domain antibody, which can bind to PD-L1 and block the binding of PD-L1/PD-1.

SUMMARY OF INVENTION

The present invention provides a single-domain antibody specifically against PD-L1 and a tetravalent form thereof, which can effectively block the binding of PD-L1 and PD-1.

In a first aspect of the present invention, it provides complementarity determining regions (or CDRs) of an anti-PD-L1 single-domain antibody VHH chain, wherein the complementarity determining regions of the VHH chain comprise:

CDR1 as shown in SEQ ID No: 5, CDR2 as shown in SEQ ID No: 6, and CDR3 as shown in SEQ ID No: 7.

In another preferred embodiment, the CDR1, CDR2 and CDR3 are separated by the framework regions FR1, FR2, FR3 and FR4 of the VHH chain.

In a second aspect of the present invention, it provides a VHH chain of an anti-PD-L1 single-domain antibody, wherein the VHH chain comprises framework regions or FRs and the complementarity determining regions or CDRs according to the first aspect of the present invention.

In another preferred embodiment, the framework regions or FRs are selected from the group consisting of:
(a) FR1 as shown in SEQ ID No: 1, FR2 as shown in SEQ ID No: 2, FR3 as shown in SEQ ID No: 3, and FR4 as shown in SEQ ID No: 4; and
(b) FR1 as shown in SEQ ID No: 10, FR2 as shown in SEQ ID No: 11, FR3 as shown in SEQ ID No: 12, and FR4 as shown in SEQ ID No: 13.

In another preferred embodiment, the VHH chain of the anti-PD-L1 single-domain antibody is shown in SEQ ID No: 8 or 14.

In a third aspect of the present invention, it provides an anti-PD-L1 single-domain antibody, which is a single-domain antibody targeting PD-L1 epitope and has a VHH chain according to the second aspect of the present invention.

In another preferred embodiment, the single-domain antibody comprises monomer and/or divalent and/or tetravalent form.

In another preferred embodiment, the single-domain antibody has a VHH chain whose amino acid sequence is as shown in SEQ ID No: 8 and/or SEQ ID No: 14.

In a fourth aspect of the present invention, it provides an anti-PD-L1 single-domain antibody, wherein the PD-L1 single-domain antibody (P) has the following elements from N-terminus to C-terminus:
A-Fc;
wherein,
element A is a sequence as shown in SEQ ID No: 14;
"—" represents a peptide bond.

In another preferred embodiment, the amino acid sequence of the anti-PD-L1 single-domain antibody is as shown in SEQ ID No: 16.

In another preferred embodiment, IgG is derived from human.

In the fifth aspect of the present invention, it provides an anti-PD-L1 single-domain antibody in tetravalent form, which has the following structure:
A-L-P~P-L-A;
wherein,
element P is a PD-L1 single-domain antibody according to the third aspect of the invention,
element A is a sequence as shown in SEQ ID No: 14;
L represents a linker;
"—" represents a peptide bond; and
"~" represents a disulfide bond.

In another preferred embodiment, the linker is selected from the following sequence: $(G_aS_b)_x$-$(G_mS_n)_y$, where each of a, b, m, n, x, and y is 0, 1, 2, 3, 4, 5, 6, 7, 8, 9 or 10 (preferably, a=4 and b=1).

In another preferred embodiment, the amino acid sequence of the tetravalent PD-L1 single-domain antibody is as shown in SEQ ID No:18.

In the sixth aspect of the present invention, it provides a polynucleotide or a combination thereof, which encodes one or more proteins selected from the group consisting of: the CDR regions of the anti-PD-L1 single-domain antibody VHH chain according to the first aspect of the present invention, the VHH chain of the anti-PD-L1 single-domain antibody according to the second aspect of the invention, the anti-PD-L1 single-domain antibody of the third aspect of the invention, and the tetravalent antibody according to the fifth aspect of the invention.

In another preferred embodiment, the polynucleotide is selected from one or more of the following group: a nucleotide sequence as shown in SEQ ID No: 9, 15, or 19.

In another preferred embodiment, the nucleotide sequence of SEQ ID No: 19 encodes an amino acid sequence of antibody as shown in SEQ ID No: 18.

In another preferred embodiment, the polynucleotide includes DNA or RNA.

In the seventh aspect of the present invention, it provides a PD-L1 single-domain antibody which is composed of the VHH amino acid sequence shown in SEQ ID No: 14 fused with the human immunoglobulin IgG1 amino acid sequence, and the amino acid sequence of the PD-L1 single-domain antibody is shown in SEQ ID No: 16.

In the eighth aspect of the present invention, it provides a linker for connecting single-domain antibody, wherein the linker consists of an amino acid sequence as shown in SEQ ID No: 17.

In the ninth aspect of the present invention, it provides a humanized tetravalent anti-PD-L1 single-domain antibody, wherein the tetravalent antibody is formed by linking the anti-PD-L1 single-domain antibody as shown in SEQ ID No: 14 and the PD-L1 single-domain antibody as shown in SEQ ID No: 16 with the linker according to the sixth aspect; and the amino acid sequence of the humanized tetravalent anti-PD-L1 single-domain antibody is shown in SEQ ID No: 18; accordingly, the polynucleotide sequence of the tetravalent antibody is shown in SEQ ID No: 19.

In the tenth aspect of the present invention, it provides an expression vector containing the polynucleotide or a combination thereof according to the sixth aspect of the present invention.

In the eleventh aspect of the present invention, it provides a host cell which contains the expression vector of the tenth aspect of the present invention, or whose genome has been incorporated the polynucleotide or a combination thereof according to the sixth aspect of the present invention.

In another preferred embodiment, the host cell is selected from the group consisting of: a mammalian cell, *E. coli*, a yeast cell, and bacteriophage.

In another preferred embodiment, the prokaryotic cell is selected from the group consisting of: *Escherichia coli, Bacillus subtilis, Lactobacillus, Streptomyces, Proteus mirabilis*, and a combination thereof. The eukaryotic cell is selected from the group consisting of: fungus such as *Pichia pastoris, Saccharomyces cerevisiae, Schizosaccharomyces pombe, Trichoderma*; an insect cell such as a grass armyworm cell; a plant cell such as a tobacco cell; a mammalian cell such as a BHK cell, a CHO cell, a COS cell, a myeloma cell, and the like. In another preferred embodiment, the host cell is preferably a mammalian cell, and more preferably an HEK293 cell, CHO cell, BHK cell, NSO cell, or COS cell.

In the twelfth aspect of the present invention, it provides a method for producing an anti-PD-L1 single-domain antibody or a derivative protein thereof, which comprises the steps of:
(a) cultivating the host cell according to the eleventh aspect of the present invention under conditions suitable for the production of a single-domain antibody and the derivative protein thereof, thereby obtaining a culture containing the anti-PD-L1 single-domain antibody or the derivative protein thereof; and
(b) isolating or recovering the anti-PD-L1 single-domain antibody or the derivative protein thereof from the culture; and optionally
(c) separating and/or purifying the anti-PD-L1 single-domain antibody obtained in Step (b).

In the thirteenth aspect of the present invention, it provides a conjugate which contains:
(a) the VHH chain of the anti-PD-L1 single-domain antibody according to the second aspect of the present invention, or the anti-PD-L1 single-domain antibody according to the third aspect of the present invention, or the anti-PD-L1 single-domain antibody according to the fourth aspect of the present invention, or the humanized tetravalent anti-PD-L1 single-domain antibody according to the ninth aspect of the present invention; and
(b) a modified label moiety selected from the group consisting of:
(b) a modified label selected from the group consisting of a chemical label and a biomarker.

In another preferred example, the conjugate is a conjugate prepared by linking the chemical label or the biomarker with the anti-PD-L1 single-domain antibody.

In another preferred example, the chemical label is isotope, immunotoxin and/or chemical drug.

In another preferred example, the biomarker is biotin, avidin, or enzyme label.

In the fourteenth aspect of the present invention, it provides an immunoconjugate formed by coupling the anti-PD-L1 single-domain antibody of the third aspect of the present invention or the conjugate of the thirteenth aspect of the present invention to a solid support or semi-solid support.

In another preferred example, the immunoconjugate comprises: a fluorescent or luminescent marker, radioactive marker, MRI (magnetic resonance imaging) or CT (electronic computer X-ray tomography) contrast agent, or enzyme capable of producing a detectable product, radionuclide, biotoxin, cytokine (such as IL-2, etc.), antibody, antibody Fc fragment, antibody scFv fragment, gold nanoparticle/nanorod, virus particle, liposome, nanomagnetic particle, prodrug activating enzyme (e.g., DT-diaphorase (DTD) or biphenyl hydrolase-like protein (BPHL)), chemotherapeutic agent (e.g., cisplatin), or nanoparticle in any form, etc.

In another preferred embodiment, the immunoconjugate contains: a multivalent VHH chain of the anti-PD-L1 single-domain antibody according to the second aspect of the present invention, the anti-PD-L1 single-domain antibody according to the third aspect of the present invention, the anti-PD-L1 single-domain antibody according to the seventh aspect of the present invention, or a humanized tetravalent anti-PD-L1 single-domain antibody according to the ninth aspect of the invention.

In another preferred embodiment, the multivalent means that the amino acid sequence of the immunoconjugate contains multiple repeats of the VHH chain of the anti-PD-L1 single-domain antibody according to the second aspect of the present invention, the anti-PD-L1 single-domain antibody according to the third aspect of the present invention, or the anti-PD-L1 single-domain antibody according to the seventh aspect of the present invention, or a humanized tetravalent anti-PD-L1 single-domain antibody according to the ninth aspect of the invention.

In the fifteenth aspect of the present invention, it provides a use of the anti-PD-L1 single-domain antibody according to the third aspect of the present invention, the conjugate according to the thirteenth aspect of the present invention, and/or the immunoconjugate according to the fourteenth aspect of the present invention in preparation of (a) a reagent for detecting a PD-L1 molecule; (b) a medicine for treating a tumor.

In the sixteenth aspect of the present invention, it provides a kit comprising one or more substances selected from the group consisting of the anti-PD-L1 single-domain antibody according to the third aspect of the present invention, the conjugate according to the thirteenth aspect of the invention, or the immunoconjugate according to the fourteenth aspect of the invention.

In the seventeenth aspect of the invention, it provides a use of the anti-PD-L1 single-domain antibody according to the third aspect of the invention, the anti-PD-L1 single-domain antibody according to the fourth aspect or the seventh aspect of the invention, and the tetravalent anti-PD-L1 single-domain antibody according to the ninth aspect of the invention, or a antigen-binding fragment thereof, in preparation of a formulation that blocks the binding of PD-L1 and PD-1.

In an eighteenth aspect of the present invention, it provides a pharmaceutical composition comprising:
(i) one or more substance selected from the anti-PD-L1 single-domain antibody according to the third aspect of the present invention, the anti-PD-L1 single-domain antibody according to the fourth or seventh aspect of the present invention, the tetravalent anti-PD-L1 single-domain antibody according to the fifth or ninth aspect of the present invention, or the immunoconjugate according to the fourteenth aspect of the present invention; and (ii) a pharmaceutically acceptable carrier.

In another preferred embodiment, the pharmaceutical composition is in the form of an injection.

In another preferred embodiment, the pharmaceutical composition is used for preparing a medicine for treating a tumor, and the tumor is selected from the group consisting of: gastric cancer, liver cancer, leukemia, renal carcinoma, lung cancer, carcinoma of small intestine, bone cancer, prostate carcinoma, colorectal cancer, breast cancer, colon cancer, prostate carcinoma, cervical cancer, lymphoma, adrenal tumor, and bladder tumors.

In the nineteenth aspect of the present invention, it provides a method for in vitro non-diagnostic and/or diagnostic detection of PD-L1 protein in a sample, which comprises the steps of:
(1) contacting the sample with the anti-PD-L1 single-domain antibody of the third aspect of the invention, or the anti-PD-L1 single-domain antibody of the fourth or seventh aspect of the invention, or the tetravalent anti-PD-L1 single-domain antibody according to the fifth or the ninth aspect of the invention;
(2) detecting whether an antigen-antibody complex is formed, wherein the formation of the complex indicates the presence of PD-L1 protein in the sample.

In the twentieth aspect of the present invention, it provides one or more uses of the anti-PD-L1 single-domain antibody of the present invention:
(i) for the detection of a human PD-L1 molecule;
(ii) for the flow cytometry detection;
(iii) for the cellular immunofluorescence detection;
(iv) for the treatment of a tumor;
(v) for the tumor diagnosis.

In another preferred embodiment, the use is non-diagnostic and non-therapeutic.

In the twenty-first aspect of the present invention, it provides a recombinant protein, which has:
(i) the sequence of the heavy chain variable region VHH according to the second aspect of the present invention, or the sequence of the single-domain antibody according to the third aspect of the present invention, the anti-PD-L1 single-domain antibody according to the seventh aspect of the present invention or the tetravalent anti-PD-L1 single-domain antibody according to the ninth aspect of the present invention; and
(ii) an optional tag sequence to aid expression and/or purification..

In another preferred embodiment, the tag sequence comprises a 6His tag, and an HA tag.

In another preferred embodiment, the recombinant protein specifically binds to PD-L1 protein.

In the twenty-second aspect of the present invention, it provides a use of the VHH chain according to the second aspect of the present invention, the single-domain antibody according to the third aspect of the present invention, the anti-PD-L1 single-domain antibody according to the seventh aspect, the tetravalent anti-PD-L1 single-domain antibody according to the ninth aspect of the present invention, or the immunoconjugate according to the fourteenth aspect of the present invention for the preparation of a medicament, reagent, detection plate or kit;
wherein the reagent, detection plate or kit is used for detecting PD-L1 protein in a sample;

wherein the medicament is used for treating or preventing a tumor expressing PD-L1 protein (i.e., PD-L1 positive).

In another preferred embodiment, the tumor comprises: melanoma, gastric cancer, lymphoma, liver cancer, leukemia, renal carcinoma, lung cancer, carcinoma of small intestine, bone cancer, prostate carcinoma, colorectal cancer, breast cancer, colon cancer, prostate carcinoma, and adrenal tumor.

In the twenty-third aspect of the present invention, it provides a method for detecting PD-L1 protein in a sample, which comprises the steps of:
(1) contacting the sample with the single-domain antibody of the present invention or the anti-PD-L1 single-domain antibody according to the seventh aspect, the tetravalent anti-PD-L1 single-domain antibody according to the ninth aspect of the present invention;
(2) detecting whether an antigen-antibody complex is formed, wherein the formation of the complex indicates the presence of PD-L1 protein in the sample.

In the twenty-fourth aspect of the present invention, it provides a method of treating a disease, which comprises: administering to a subject in need the single-domain antibody according to the third aspect of the present invention, the anti-PD-L1 single-domain antibody according to the seventh aspect, the tetravalent anti-PD-L1 single-domain antibody according to the ninth aspect of the present invention, or the immunoconjugate according to the fourteenth aspect of the present invention.

In the twenty-fifth aspect of the present invention, it provides a method of treating a tumor, which comprises: administering to a subject in need the pharmaceutical composition according to the eighteenth aspect of the present invention, In another preferred embodiment, the subject includes a mammal, such as human.

It should be understood that, within the scope of the present invention, the technical features specifically described above and below (such as the Examples) can be combined with each other, thereby constituting a new or preferred technical solution which needs not be redundantly described one by one.

DESCRIPTION OF DRAWING

FIG. 10 shows the ELISA detection of species specificity before and after humanization of anti-PD-L1 single-domain antibody. It showed that, before and after humanization, the bivalent anti-PD-L1 single-domain antibody only interacted with human and monkey PD-L1 but not with mouse PD-L1, and did not recognize human PD-L2 or human B7H3 or B7H4. The candidate single-domain antibody had excellent species specificity.

FIG. 11 shows the purity of the humanized tetravalent anti-PD-L1 single-domain antibody expressed in HEK293F system as detected by SEC-HPLC. The results showed that the purity of the humanized tetravalent anti-PD-L1 single-domain antibody was 99.07%.

DETAILED DESCRIPTION OF INVENTION

Figure 1:
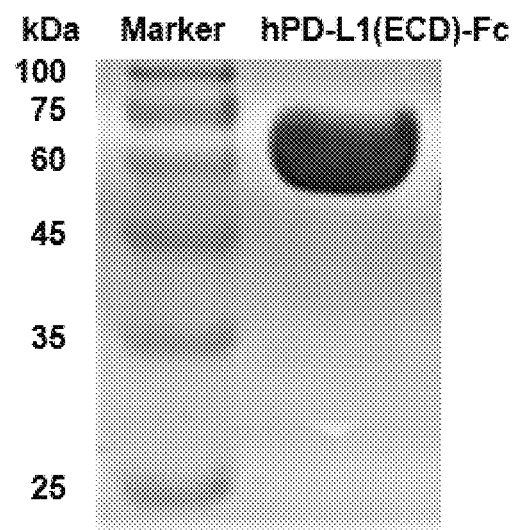
FIG. 1 shows a SDS-PAGE diagram of an antigen protein, wherein marker is a pre-stained protein standard, and the purified hPD-L1(ECD)-Fc protein is expressed by an HEK293F cell with a purity of more than 95%.

Through the extensive and intensive research and a lot of screening, the present inventor has successfully obtained a class of anti-PD-L1 single-domain antibodies. The experimental results show that the obtained anti-PD-L1 single-domain antibody can effectively block the interaction between PD-L1 and PD-1, and the humanized anti-PD-L1 single-domain antibody can also effectively block the binding of PD-L1 and PD-1. The blocking activity of the tetravalent antibody constructed on this basis is significantly better than that of the control antibody Atezolizumab. Based on these results, the inventors have completed the present invention.

Specifically, in the present invention, the human PD-L1 extracellular domain as an antigen protein was utilized to immunize camels to obtain a high-quality immune single-domain antibody gene library, and then the PD-L1 protein molecule was coupled onto the ELISA plate to display the correct spatial structure of the PD-L1 protein. The antigen in this form was used in the phage display technology to screen the immune single-domain antibody gene library (camel heavy chain antibody phage display gene library) to obtain the PD-L1 specific single-domain antibody gene. The obtained gene was then transferred into E. coli to obtain a single-domain antibody species that could be efficiently expressed in E. coli and had high specificity.

As used herein, the terms "single-domain antibody of the present invention", "anti-PD-L1 single-domain antibody of the present invention", and "PD-L1 single-domain antibody of the present invention" can be used interchangeably and refer to a single-domain antibody that specifically recognizes and binds PD-L1 (including human PD-L1). Particularly preferred is a single-domain antibody whose amino acid sequence of the VHH chain is shown in SEQ ID Nos: 8 or 14.

As used herein, the term "antibody" or "immunoglobulin" is a heterotetrameric glycoprotein of about 150,000 Daltons with the same structural characteristics, which consists of two identical light chains (L) and two identical heavy chains (H). Each light chain is connected to the heavy chain through a covalent disulfide bond, and the number of disulfide bonds between heavy chains of different immunoglobulin isotypes is different. Each heavy and light chain also has regularly spaced disulfide bonds in the chain. Each heavy chain has a variable region (VH) at one end, followed by multiple constant regions. Each light chain has a variable region (VL) at one end and a constant region at the other end. The constant region of the light chain is opposite to the first constant region of the heavy chain, and the variable region of the light chain is opposite to the variable region of the heavy chain. Special amino acid residues form an interface between the variable regions of the light chain and the heavy chain.

As used herein, the terms "single-domain antibody", "VHH", and "nanobody" have the same meaning and can be used interchangeably, and refer to the variable region of a cloned antibody heavy chain, which constructs a single-domain antibody (VHH) consisting of only one heavy chain variable region, and is the smallest antigen-binding fragment with complete functions. Usually, an antibody that naturally lacks the light chain and the heavy chain constant region 1 (CH1) is first obtained, and then the variable region of the antibody heavy chain is cloned, so as to construct a single-domain antibody (VHH) consisting of only one heavy chain variable region.

As used herein, the term "variable" means that certain parts of the variable region in an antibody differ in sequence, which forms the binding and specificity of various specific antibodies for their specific antigens. However, the variability is not evenly distributed throughout the variable region of the antibody. It is concentrated in three segments called complementarity determining regions (CDRs) or hypervariable regions in the light chain variable regions and heavy chain variable regions. The more conserved part of the variable region is called the framework region (FR). The variable regions in the natural heavy and light chains each contain four FR regions, which are roughly in the β-fold configuration, connected by the three CDRs that form the connecting loop, and in some cases part of the β-folded structure may be formed. The CDRs in each chain are closely together through the FR regions and together with the CDRs of the other chain to form the antigen-binding site of the antibody (see Kabat et al., NIH Publ. No. 91-3242, Volume I, pages 647-669) (1991)). The constant regions are not directly involved in the binding of antibodies to antigens, but they exhibit different effector functions, such as antibody-dependent cytotoxicity involved in antibodies.

As known to those skilled in the art, immunoconjugates and fusion expression products include: conjugates formed by combining drugs, toxins, cytokines, radionuclides, enzymes, and other diagnostic or therapeutic molecules with the antibodies or fragments thereof of the present invention. The present invention also includes cell surface markers or antigens that bind to the anti-PD-L1 antibody or fragments thereof.

As used herein, the terms "heavy chain variable region" and "$V_H$" can be used interchangeably.

As used herein, the terms "variable region" and "complementarity determining region (CDR)" can be used interchangeably.

In a preferred embodiment of the present invention, the heavy chain variable region of the antibody includes three complementarity determining regions CDR1, CDR2, and CDR3.

In a preferred embodiment of the present invention, the heavy chain of the antibody includes the above heavy chain variable region and heavy chain constant region.

In the present invention, the terms "antibody of the present invention", "protein of the present invention", or "polypeptide of the present invention" can be used interchangeably, and refer to a polypeptide that specifically binds to the PD-L1 protein, such as a protein or polypeptide having a heavy chain variable region. They may or may not contain a starting methionine.

The present invention also provides other proteins or fusion expression products comprising the antibodies of the present invention. Specifically, the present invention includes any protein or protein conjugate and fusion expression product having a heavy chain containing a variable region (i.e., immunoconjugate and fusion expression product), as long as the variable region is the same as the heavy chain variable region of the antibody of the present invention or has at least 90%, preferably at least 95% homology.

In general, the antigen-binding properties of antibodies can be described by three specific regions located in the variable region of the heavy chain, called variable regions (CDR). The segment is divided into 4 framework regions (FR), the amino acid sequences of the 4 FRs are relatively conservative, and do not directly participate in the binding reaction. These CDRs form a circular structure, and are close to each other in space structure via the β-fold formed by the FRs therebetween. The CDRs on the heavy chain and the CDRs on the corresponding light chain constitute the antigen binding site of the antibody. The amino acid sequences of antibodies of the same type can be compared to determine which amino acids constitute the FR or CDR regions.

The variable regions of heavy chains of the antibodies of the present invention are of particular interest because at least part of them are involved in binding antigens. Therefore, the present invention includes those molecules having a CDR-containing antibody heavy chain variable region, as long as their CDRs have more than 90% (preferably more than 95%, most preferably more than 98%) homology with the CDRs identified herein.

The present invention includes not only whole antibodies, but also fragments of antibodies with immunological activity or fusion proteins formed by antibodies and other sequences. Therefore, the present invention also includes fragments, derivatives and analogs of the antibodies.

As used herein, the terms "fragment", "derivative" and "analog" refer to a polypeptide that substantially retains the same biological function or activity of the antibody of the present invention. The polypeptide fragment, derivative or analog of the present invention may be (i) a polypeptide having one or more conservative or non-conservative amino acid residues (preferably conservative amino acid residues) substituted, and such substituted amino acid residues may or may not be encoded by the genetic code, or (ii) a polypeptide with a substitution group in one or more amino acid residues, or (iii) a polypeptide formed by the fusion of a mature polypeptide with another compound (such as a compound that extends the half-life of the polypeptide, such as polyethylene glycol), or (iv) a polypeptide formed by fusing the additional amino acid sequence to the polypeptide sequence (such as a leader sequence or secretion sequence or a sequence or proprotein sequence used to purify the polypeptide, or a fusion protein formed with a 6His tag). According to the teachings herein, these fragments, derivatives and analogs are within the scope of those skilled in the art.

The antibody of the present invention refers to a polypeptide having PD-L1 protein binding activity and containing the above-mentioned CDR regions. The term also includes variant forms of polypeptides containing the above CDR regions that have the same function as the antibodies of the present invention. These variant forms include (but are not limited to): one or more amino acid deletions, insertions and/or substitutions, and one or several amino acids addition to the C-terminal and/or N-terminal. For example, in the art, the substitution of amino acids with close or similar properties usually does not change the function of the protein. As another example, adding one or several amino acids to the C-terminus and/or N-terminus usually does not change the function of the protein. The term also includes active fragments and active derivatives of the antibodies of the present invention.

The variant forms of the polypeptide include: homologous sequences, conservative variants, allelic variants, natural mutants, induced mutants, proteins encoded by DNA that can hybridize with DNA encoding the antibody of the present invention under highly or lowly stringent conditions, and polypeptides or proteins obtained using antiserum against antibodies of the present invention.

The present invention also provides other polypeptides, such as fusion proteins comprising single-domain antibodies or fragments thereof. In addition to almost full-length polypeptides, the present invention also includes fragments of single-domain antibodies of the present invention. Generally, the fragment has at least about 50 consecutive amino acids, preferably at least about 50 consecutive amino acids, more preferably at least about 80 consecutive amino acids, and most preferably at least about 100 consecutive amino acids of the antibody of the present invention.

In the present invention, "conservative variant of the antibody of the present invention" refers to that based on the amino acid sequence of the antibody of the present invention, at most 10, preferably at most 8, more preferably at most 5, and most preferably at most 3 amino acids are replaced by amino acids with similar or close properties to form a polypeptide. Preferably, these conservative variant polypeptides are produced by amino acid substitution according to Table 1.

TABLE 1

| Original residue | Representative substitution | Preferred substitution |
|---|---|---|
| Ala(A) | Val; Leu; Ile | Val |
| Arg(R) | Lys; Gln; Asn | Lys |
| Asn(N) | Gln; His; Lys; Arg | Gln |
| Asp(D) | Glu | Glu |
| Cys(C) | Ser | Ser |
| Gln(Q) | Asn | Asn |
| Glu(E) | Asp | Asp |
| Gly(G) | Pro; Ala | Ala |
| His(H) | Asn; Gln; Lys; Arg | Arg |
| Ile(I) | Leu; Val; Met; Ala; Phe | Leu |
| Leu(L) | Ile; Val; Met; Ala; Phe | Ile |
| Lys(K) | Arg; Gln; Asn | Arg |
| Met(M) | Leu; Phe; Ile | Leu |
| Phe(F) | Leu; Val; Ile; Ala; Tyr | Leu |
| Pro(P) | Ala | Ala |
| Ser(S) | Thr | Thr |
| Thr(T) | Ser | Ser |
| Trp(W) | Tyr; Phe | Tyr |
| Tyr(Y) | Trp; Phe; Thr; Ser | Phe |
| Val(V) | Ile; Leu; Met; Phe; Ala | Leu |

The present invention also provides polynucleotide molecules encoding the above antibodies or fragments or fusion proteins thereof. The polynucleotide of the present invention may be in the form of DNA or RNA. DNA forms include cDNA, genomic DNA, or synthetic DNA. DNA can be single-stranded or double-stranded. DNA can be a coding strand or a non-coding strand.

The polynucleotide encoding the mature polypeptide of the present invention includes: a coding sequence encoding only the mature polypeptide; a coding sequence encoding the mature polypeptide with various additional coding sequences; a coding sequence encoding the mature polypeptide (and optional additional coding sequences) with a non-coding sequence.

The term "polynucleotide encoding a polypeptide" may include a polynucleotide encoding the polypeptide, or a polynucleotide further containing additional coding and/or non-coding sequences.

The present invention also relates to polynucleotides that hybridize to the above-mentioned sequences and have at least 50%, preferably at least 70%, and more preferably at least 80% identity between the two sequences. The present invention particularly relates to polynucleotides that can hybridize to the polynucleotides of the present invention under stringent conditions. In the present invention, "stringent conditions" means: (1) hybridization and elution at lower ionic strength and higher temperature, such as 0.2× SSC, 0.1% SDS, 60° C.; or (2) denaturing agent, such as 50% (v/v) formamide, 0.1% calf serum/0.1% Ficoll, 42° C., etc. is added during hybridization; or (3) hybridization occurs only when the identity between the two sequences is at least 90%, and more preferably at least 95%. Furthermore, the polypeptide encoded by the hybridizable polynucleotide has the same biological function and activity as the mature polypeptide.

The full-length nucleotide sequence of the antibody of the present invention or a fragment thereof can generally be obtained by PCR amplification method, recombination method or artificial synthesis method. A feasible method is to use synthetic methods to synthesize the relevant sequences, especially when the fragment length is short. Generally, a fragment with a very long sequence can be obtained by synthesizing multiple small fragments and then connecting them. In addition, the coding sequence of the heavy chain and the expression tag (such as 6His) can also be fused together to form a fusion protein.

Once the relevant sequence is obtained, the relevant sequence can be obtained in large quantities by the recombination method. This is usually done by cloning it into a vector, then transferring it into a cell, and then isolating the relevant sequence from the propagated host cell by conventional methods. The biomolecules (nucleic acids, proteins, etc.) involved in the present invention include biomolecules that exist in an isolated form.

At present, the DNA sequence encoding the protein (or a fragment or a derivative thereof) of the present invention can be obtained completely by chemical synthesis. This DNA sequence can then be introduced into various existing DNA molecules (or vectors) and cells known in the art. In addition, mutations can also be introduced into the protein sequence of the present invention by chemical synthesis.

The present invention also relates to vectors containing the appropriate DNA sequence as described above and an appropriate promoter or regulatory sequence. These vectors can be used to transform appropriate host cells so that they can express proteins.

The host cell may be a prokaryotic cell, such as a bacterial cell; or a lower eukaryotic cell, such as a yeast cell; or a higher eukaryotic cell, such as a mammalian cell. Representative examples are bacterial cells such as *Escherichia coli, Streptomyces*, or *Salmonella typhimurium*; fungal cells such as yeast; insect cells such as *Drosophila* S2 or Sf9; animal cells such as CHO, COST, 293 cells, etc.

Transformation of host cells with recombinant DNA can be performed using conventional techniques well known to those skilled in the art. When the host is a prokaryotic organism such as *E. coli*, competent cells that can absorb DNA can be harvested after the exponential growth phase and treated with the $CaCl_2$ method. The procedures used are well known in the art. Another method is to use $MgCl_2$. If necessary, transformation can also be carried out by electroporation. When the host is an eukaryote, the following DNA transfection methods can be used: calcium phosphate co-precipitation method, conventional mechanical methods such as microinjection, electroporation, liposome packaging, etc.

The obtained transformant can be cultured by a conventional method to express the polypeptide encoded by the gene of the present invention. Depending on the host cell used, the medium used in the culture can be selected from various conventional mediums. The cultivation is carried out under conditions suitable for the growth of host cells. When the host cell grows to an appropriate cell density, the selected promoter is induced by an appropriate method (such as temperature conversion or chemical induction), and the cell is cultured for a period of time.

The recombinant polypeptide in the above method may be expressed in a cell or on a cell membrane, or secreted out of the cell. If necessary, the recombinant protein can be isolated and purified by various separation methods using its physical, chemical and other characteristics. These methods are well known to those skilled in the art. Examples of these methods include, but are not limited to: conventional renaturation treatment, treatment with protein precipitation agent (salting out method), centrifugation, disruption of bacteria through penetration, ultra-treatment, ultra-centrifugation, molecular sieve chromatography (gel filtration), adsorption chromatography, ion exchange chromatography, high performance liquid chromatography (HPLC) and various other liquid chromatography techniques and combinations of these methods.

The antibody of the present invention may be used alone, or may be combined or coupled with a detectable label or marker (for diagnostic purposes), a therapeutic agent, a PK (protein kinase) modification moiety, or a combination thereof.

Detectable markers for diagnostic purposes include, but are not limited to: fluorescent or luminescent markers, radioactive markers, MRI (magnetic resonance imaging) or CT (electronic computer X-ray tomography) contrast agents, or an enzyme capable of producing a detectable product.

Therapeutic agents that can be combined or conjugated with the antibodies of the present invention include, but are not limited to: 1. radionuclides; 2. biotoxin; 3. cytokines such as IL-2, etc.; 4. gold nanoparticles/nanorods; 5. viruses particles; 6. liposomes; 7. magnetic nanosphere; 8. drug-activating enzymes (e.g., DT-diaphorase (DTD) or biphenylhydrolase-like protein (BPHL)); 9. chemotherapeutic agents (e.g., cis-platinum) or any form of nanoparticles, etc.

FUSION PROTEIN AND TETRAVALENT ANTIBODY

The fusion protein of the present invention refers to a single-chain structural protein formed by fusion of the VHH chain of the present invention or a single-domain antibody containing the CDRs of the present invention and a human IgG Fc fragment. Specifically, the fusion protein (P) of the present invention has the following structure from N-terminus to C-terminus:

A-Fc;

wherein, element A is a sequence as shown in SEQ ID NO: 14;

"—" represents a peptide bond.

A preferred amino acid sequence of the fusion protein of the present invention is shown in SEQ ID NO: 16, or an amino acid sequence or an active fragment thereof having at least 90%, 91%, 92%, 93%, 94%, 95%, 96%, 97%, 98%, or 99% identity.

After the fusion protein is formed, the fusion protein of the present invention can be further combined with the sequence shown in SEQ ID NO: 14 (element A) through a linker (L) to form a bivalent antibody.

The linker useful in the fusion protein of the present invention has no particular limitation, and can be any connection sequence that connects the sequence shown in SEQ ID NO: 14 (element A) to the fusion protein (element P) of the present invention without affecting the structures and folding of the two elements. Preferably, linker useful in the present invention includes: GGGSGGGS, GS, (GGGGS)n, wherein n=1 or 2 or 3 or 4.

In addition, the bivalent antibody of the present invention can be connected by disulfide bonds between Fc fragments, thereby forming a tetravalent antibody having the following structure:

A-L-P~P-L-A;

wherein, element P is the fusion protein of the third aspect of the present invention, element A is the sequence as shown in SEQ ID NO: 14;

L represents a linker;

"—" represents a peptide bond;

"~" represents a disulfide bond.

A preferred tetravalent antibody of the present invention is as shown in SEQ ID NO: 18, or an amino acid sequence or an active fragment thereof having at least 90%, 91%, 92%, 93%, 94%, 95%, 96%, 97%, 98%, or 99% identity.

The fusion protein of the present invention and the tetravalent antibody have higher blocking efficiency on PD-L1 and better binding affinity.

One particularly preferred tetravalent antibody has the amino acid sequence as shown in SEQ ID NO: 18.

PHARMACEUTICAL COMPOSITION

The present invention also provides a composition. Preferably, the composition is a pharmaceutical composition, which contains the above antibody or an active fragment or fusion protein thereof, and a pharmaceutically acceptable carrier. Generally, these substances can be formulated in a non-toxic, inert and pharmaceutically acceptable aqueous carrier medium, wherein the pH is usually about 5-8, preferably about 6-8, although the pH can vary depending on the nature of the substance being formulated and the condition to be treated. The formulated pharmaceutical composition can be administered by conventional routes, including (but not limited to): intratumoral, intraperitoneal, intravenous, or topical administration.

The pharmaceutical composition of the present invention can be directly used to bind PD-L1 protein molecules, and thus can be used to treat tumors. In addition, other therapeutic agents can be used simultaneously.

The pharmaceutical composition of the present invention contains a safe and effective amount (such as 0.001-99 wt %, preferably 0.01-90 wt %, more preferably 0.1-80 wt %) of the above single-domain antibody (or its conjugate) of the present invention and a pharmaceutically acceptable carrier or excipient. Such carriers include (but are not limited to): saline, buffer, glucose, water, glycerin, ethanol, and a combination thereof. The pharmaceutical preparation should match the mode of administration. The pharmaceutical composition of the present invention can be prepared in the form of an injection, for example, prepared by a conventional method using a physiological saline or an aqueous solution containing glucose and other adjuvants. Pharmaceutical compositions such as injections and solutions are preferably manufactured under sterile conditions. The amount of active ingredient administered is a therapeutically effective amount, for example, about 10 mg/kg body weight to about 50 mg/kg body weight per day. In addition, the polypeptide of the present invention can be used together with other therapeutic agents.

When using a pharmaceutical composition, a safe and effective amount of an immunoconjugate is administered to a mammal, wherein the safe and effective amount is usually at least about 10 μg/kg body weight, and in most cases does not exceed about 50 mg/kg body weight, preferably the dose is about from 10 mg/kg body weight to about 10 mg/kg body weight. Of course, the specific dosage should also consider factors such as the route of administration, the patient's health status, etc., which are within the skills of skilled physicians.

LABELED SINGLE-DOMAIN ANTIBODY

In a preferred embodiment of the present invention, the single-domain antibody carries a detectable label. More preferably, the label is selected from the group consisting of isotope, colloidal gold label, colored label or fluorescent label.

Colloidal gold labeling can be performed using methods known to those skilled in the art. In a preferred embodiment of the present invention, the anti-PD-L1 single-domain antibody is labeled with colloidal gold to obtain a colloidal gold labeled single-domain antibody.

The anti-PD-L1 single-domain antibody of the present invention has good specificity and high titer.

DETECTION METHOD

The present invention also relates to a method for detecting PD-L1 protein. The method steps are roughly as follows: obtaining a cell and/or tissue sample; dissolving the sample in a medium; and detecting the level of PD-L1 protein in the dissolved sample.

In the detection method of the present invention, the useful sample has no particular limitation, and a representative example is a cell-containing sample in a cell preservation solution.

KIT

The present invention also provides a kit containing the antibody (or a fragment thereof) or a detection plate of the present invention. In a preferred embodiment of the present invention, the kit further includes a container, an instruction for use, a buffer, and the like.

The present invention also provides a detection kit for detecting the level of PD-L1, which includes an antibody that recognizes the PD-L1 protein, a lysis medium for dissolving the sample, general reagents and buffers required for the detection, such as various buffers, detection markers, detection substrates, etc. The detection kit may be an in vitro diagnostic device.

APPLICATION

As described above, the single-domain antibody of the present invention has a wide range of biological application value and clinical application value, and its application involves the diagnosis and treatment of PD-L1-related diseases, basic medical research, biological research and other fields. A preferred application is PD-L1 targeting clinical diagnosis and therapy.

The main advantages of the present invention include:
(a) The single-domain antibody of the present invention is highly specific against human PD-L1 protein with correct spatial structure.
(b) The single-domain antibody and the derived protein thereof of the present invention has good blocking activity on interaction between PD-1 and PD-L1.
(c) The production of the single-domain antibody of the present invention is simple and has good stability.

The invention will be further illustrated with reference to the following specific examples. It is to be understood that these examples are only intended to illustrate the invention, but not to limit the scope of the invention. For the experimental methods in the following examples without particular conditions, they are performed under routine conditions (e.g., Sambrook et al., Molecular Cloning: A Laboratory Manual (New York: Cold Spring Harbor Laboratory Press, 1989) or as instructed by the manufacturer. Unless otherwise specified, all percentages or parts are by weight.

EXAMPLE 1: CONSTRUCTION AND SCREENING OF PD-L1 SINGLE-DOMAIN ANTIBODY LIBRARY

Library construction

Figure 2:
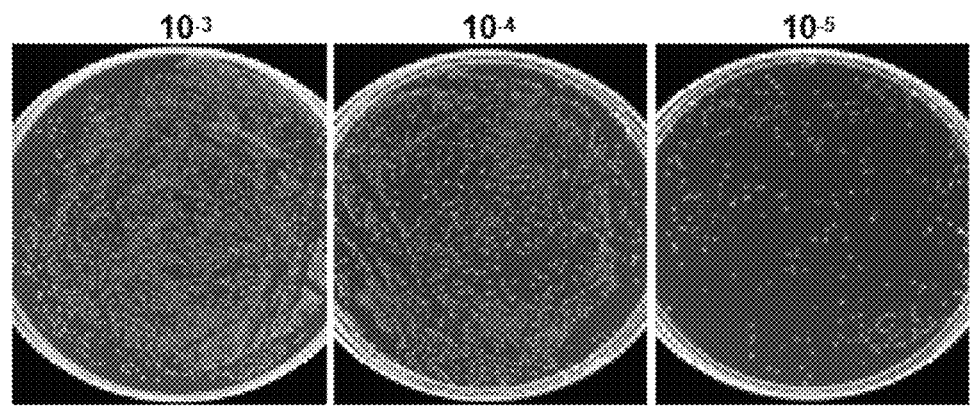
FIG. 2 shows the library capacity detection of the constructed library, wherein the constructed library is plated after gradient dilution. The figure shows the number of clones with a ⅕ gradient dilution of $10^4$-fold, $10^5$-fold, and $10^6$-fold, and the size of the library is determined by calculating the number of clone, and the library capacity of the library is calculated as $1.9 \times 10^9$ CFU.
Figure 3:
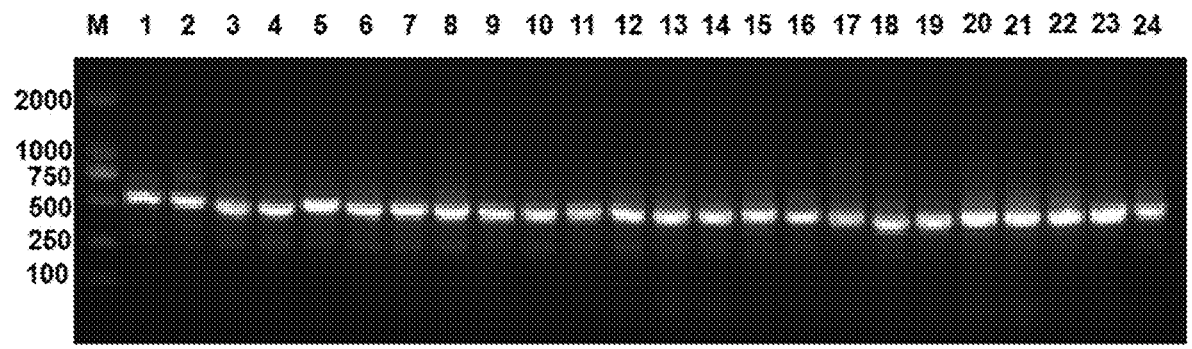
FIG. 3 shows the insertion rate detection of the library construction, showing the results of the insertion rate detection of the library construction. The DNA bands from the left to the right of the gel well are as follows: the first lane is the DNA molecular marker, and the remaining wells are the PCR products of the inserted fragments. The bands of PCR product are about 500 bp. After detection, the insertion rate of the library reaches 100%.

Briefly, (1) 1 mg of hPD-L1 (ECD)-Fc antigen was mixed with Freund's adjuvant in equal volumes and used to immunize a Xinjiang Bactrian camel once a week for a total of 7 times to stimulate B cells to express an antigen specific single-domain antibody. (2) After 7 immunizations, lymphocytes from 100 mL camel peripheral blood was isolated and total RNA was extracted. (3) cDNA was synthesized and nested PCR was performed to amplify VHH. (4) Restriction enzymes Pst I and Not I were used for the digestion of 20 µg pMECS phage display vector and 10 µg VHH and the two fragments were ligated. (5) The ligation product was transformed into electro-competent TG1 cells, thereby constructing a PD-L1 single-domain antibody library (See FIG. 2 and FIG. 3).

Figure 4:
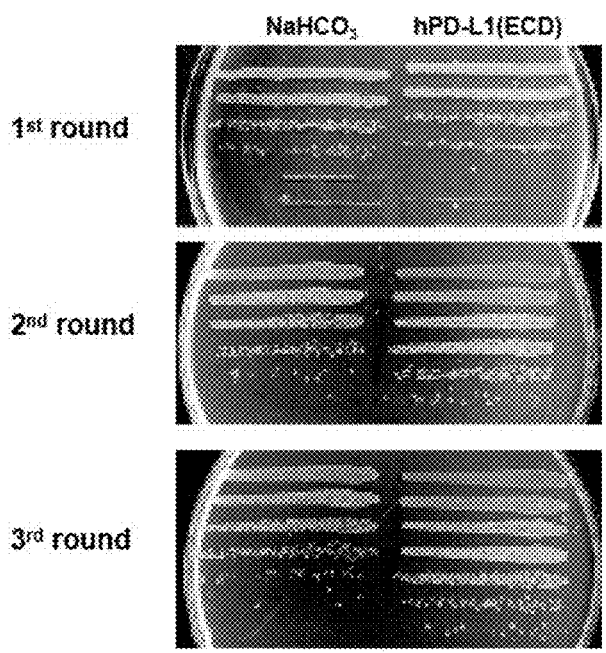
FIG. 4 shows the PD-L1 single-domain antibody screening and enrichment process. There was no enrichment in the library after the first round of panning, 11 times enrichment in the second round of panning, and 32 times enrichment in the third round of panning.

Antibody screening and identification:

(1) 10 µg hPD-L1 (ECD)-Fc antigen (10 µg Fc in NaHCO$_3$ as a control) dissolved in 100 mM NaHCO$_3$, pH 8.2 was coupled onto a NUNC ELISA Plate, and placed at 4° C. overnight. (2) 100 µL 0.1% BSA was added the next day for blocking 2 h at room temperature. (3) After 2 h, 100 µL phage (2×10$^{11}$ CFU immunized camel single-domain antibody phage display gene library) was added and placed at room temperature for 1 h. (4) 0.05% PBS+Tween-20 were used to wash 5 times so as to wash off non-specific phages. (5) The phages that specifically bound to PD-L1 were dissociated with 100 mM triethanolamine and used to infect E. coli TG1 cells in logarithmic growth phase. After incubating at 37° C. for 1 h, the phages were produced and purified for the next round of screening. The same screening process was repeated 3 to 4 rounds, thereby obtaining the enriched positive clones (FIG. 4).

Screening single Specific positive clone via phage enzyme-linked immunosorbent assay (ELISA)

(1) From the cell culture dishes containing phages from the above screening process, 200 individual colonies were picked and inoculated into TB medium containing 100 µg/mL ampicillin (1 L TB medium contained 2.3 g KH$_2$PO$_4$, 12.52 g K$_2$HPO$_4$, 12 g peptone, 24 g yeast extract, 4 mL glycerol). After cells grew to the logarithmic phase, IPTG was added with a final concentration of 1 mM and incubated overnight at 28° C. (2) A crude antibody was obtained by osmosis method and the antibody was transferred onto the antigen-coated ELISA plate, and placed at room temperature for 1 h. (3) The unbound antibody was washed off with PBST. A mouse anti-HA antibody (commercially available from Beijing Covence Biotech Company, Ltd.) was added and placed at room temperature for 1 h. (5) The unbound antibody was washed off with PBST, and a goat anti-mouse alkaline phosphatase labeled antibody was added and placed at room temperature for 1 h. (10) The unbound antibody was washed off with PBST. Alkaline phosphatase coloring solution was added and the absorbance value at 405 nm wavelength was read on the ELISA instrument. (6) When the OD value of the sample well was more than 3 times of the OD value of the control well (Ratio +/->3), it was judged as a positive clone well. The positive clone strains were sequenced and three CDR sequences of single-domain antibody were aligned and analyzed.

Figure 5:
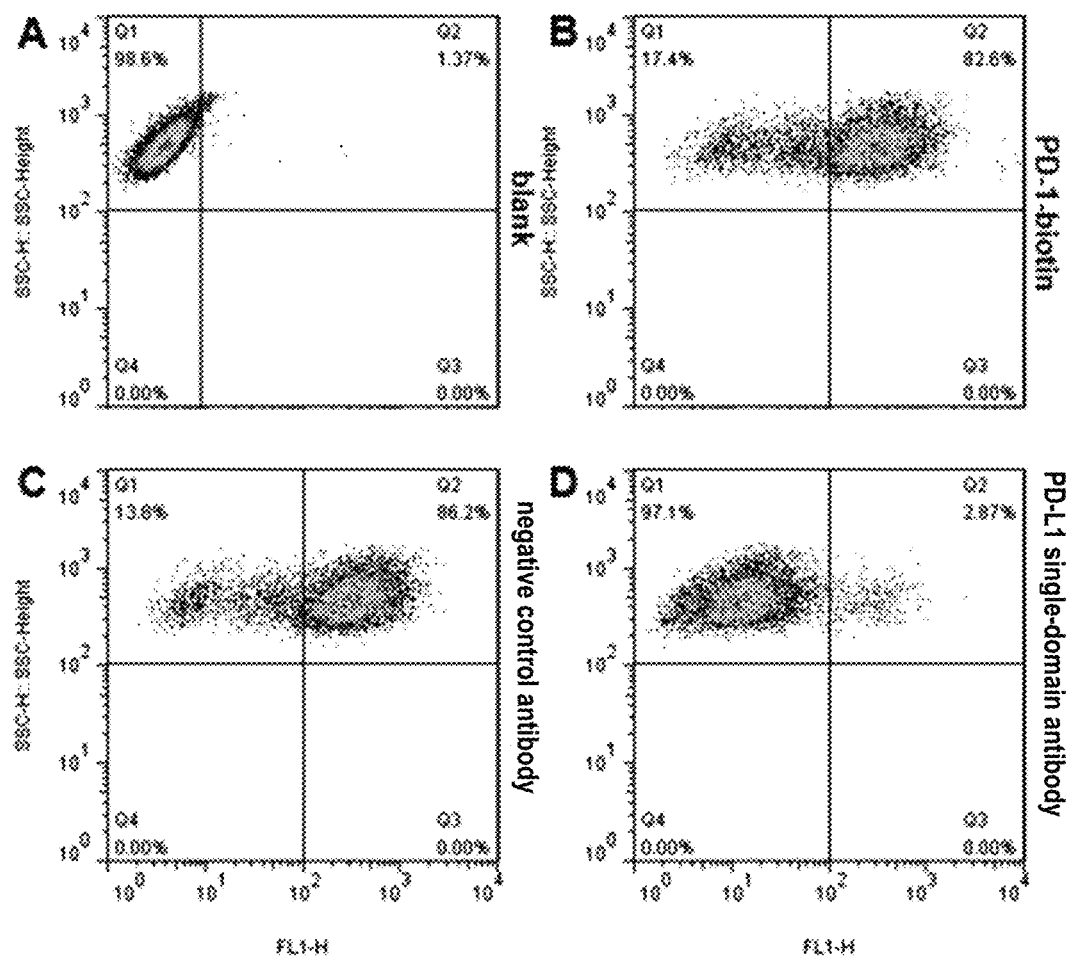
FIG. 5 shows the blocking effect of anti-PD-L1 single-domain antibody (expressed in *E. coli*) as detected by flow cytometry. The results showed that the single-domain antibody specifically against PD-L1 (the amino acid sequence of antibody was as shown in sequence ID No: 8) could block the binding of PD-L1 to PD-1.

EXAMPLE 2: DETECTION OF BLOCKING FUNCTION OF SINGLE-DOMAIN ANTIBODY VIA FLOW CYTOMETRY (1) hPD-1(ECD)-Biotin protein was prepared (The preparation of hPD-1 (ECD)-Biotin was similar to that in Example 1), wherein the method of biotinylation was according to the instructions of biotin reagent. (2) PD-L1 gene was transiently transfected into HEK293F cells to express PD-L1 protein on the cell surface. (3) The crude lysate of PD-L1 single-domain antibody TG1 strain was prepared according to Zhu Min et al., Nanoscale Res Lett., 2014 Sep 26; 9 (1): 528. (4) 1×10$^6$ HEK293F cells transiently transfected with PD-L1 were suspended in 0.5% BSA-PBS buffer, 100 µl of the above crude extract was added, and negative control (hIgG1) and positive control (Tecentriq) were set at the same time. 5 µg hPD-1(ECD)-Fc biotin was added into each well and incubated at 4° C. for 20 min. (5) The cells were washed twice with PBS, SA-PE (eBioscience Co.) was added, incubated at 4° C. for 20 min, then washed twice with PBS, and detected by flow cytometry (BD FACS Calibur). Finally, a single-domain antibody Nb27 (amino acid sequence was shown in SEQ ID No.: 8) having significant blocking effect was obtained (the results are shown in FIG. 5).

EXAMPLE 3: HUMANIZATION OF PD-L1 BLOCKING SINGLE-DOMAIN ANTIBODY (1) First, using the PD-L1 single-domain antibody sequence as shown in SEQ ID No: 8 as a template to search for the homologous structure in the structure database, and the structure in which E value=0.0 and sequence identity≥70% was used. (2) Structural comparison was performed on these structures, and according to the crystal structure resolution and the evolutionary tree constructed, multi-template homology modeling was constructed based on the PD-L1 single-domain antibody sequence as shown in SEQ ID No: 8. Then, according to the ranking of the scoring function, the structure with the lowest molpdf was selected. (3) As to the optimal structure obtained from the modeling process, the ProtSA server was used to calculate the solvent accessibility of residue, and residues greater than 40% were taken as residues exposed to solvent. (4) The optimal structure obtained from modeling process was aligned with DP-47, and the corresponding residues exposed to solvent were replaced. Finally, a humanized PD-L1 single-domain antibody with the amino acid sequence as shown in SEQ ID No. 14 was determined. The antibody sequences before and after humanization are listed in the following Table 2:

TABLE 2

| | sequence numbering (SEQ ID NO:) | |
|---|---|---|
| antibody region | Before humanization | After humanization |
| FR1 | 1 | 10 |
| CDR1 | 5 | 5 |

TABLE 2-continued

| | sequence numbering (SEQ ID NO:) | |
|---|---|---|
| antibody region | Before humanization | After humanization |
| FR2 | 2 | 11 |
| CDR2 | 6 | 6 |
| FR3 | 3 | 12 |
| CDR3 | 7 | 7 |
| FR4 | 4 | 13 |
| complete amino acid sequence | 8 | 14 |
| complete nucleotide sequence | 9 | 15 |

Figure 6:
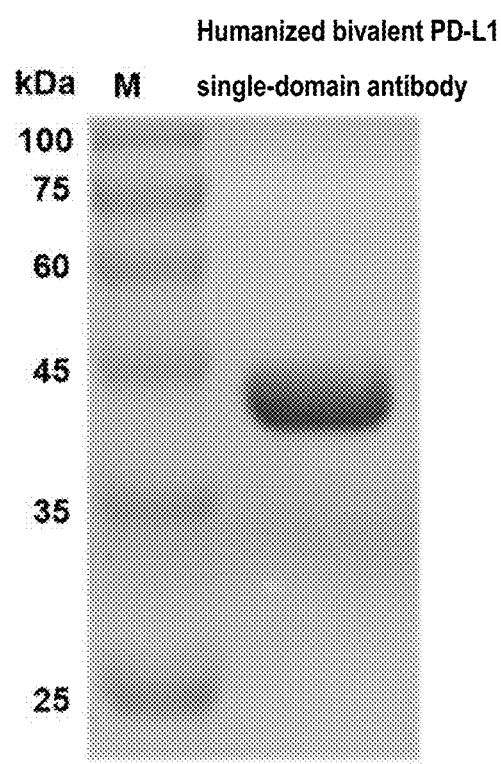
FIG. 6 shows the SDS-PAGE detection result of the humanized bivalent anti-PD-L1 single-domain antibody (SEQ ID No: 16) expressed by HEK293F system. The purity of purified humanized bivalent anti-PD-L1 single-domain antibody was more than 90%, and could be used for subsequent detection experiments.

EXAMPLE 4: EUKARYOTIC EXPRESSION AND PURIFICATION OF HUMANIZED BIVALENT PD-L1 SINGLE-DOMAIN ANTIBODY (1) The PD-L1 single-domain antibody fragments before humanization (SEQ ID NO.: 9) and after humanization (SEQ ID NO.: 15) were cloned into pFUSE-IgG1 vector, and Omega kit for large-scale extraction of plasmid was used to extract the plasmid. (2) HEK293F cells were cultured until OD was $2.0 \times 10^6$ cells/mL. (3) The plasmid and the transfection reagent PEI was well mixed at a ration of 1:3, and placed for 20 minutes, then added to HEK293F cells, which were then cultured at 37° C., 6% $CO_2$ in shaker incubator for 5-6 days. (4) The cell supernatant was collected and bound with Protein A beads at room temperature for 1 h; (5) The beads were washed with phosphate buffer (pH7.0), then 0.1M pH3.0 Glycine was used to elute the protein. (6) The eluted protein was ultrafiltrated into PBS. After measuring the yield, a sample was taken for SDS-PAGE to detect the purity (as shown in FIG. 6, the purity of the protein was more than 90%), and the remaining proteins were stored at −80° C. for subsequent experiments.

EXAMPLE 5: DETECTION OF BLOCKING EFFECT OF HUMANIZED BIVALENT PD-L1 SINGLE-DOMAIN ANTIBODY VIA FLOW CYTOMETRY (1) A375 transgenic cells which stably expressed PD-L1 were constructed. (2) For each sample, $5 \times 10^5$ PD-L1 stably transfected cells A375 were taken and placed in 0.5% BSA-PBS buffer. A serial of gradient dilution of the bivalent PD-L1 single-domain antibody before humanization and after humanization and Tecentriq positive control antibody were added, wherein the antibody gradient dilutions were 0.25 ug/mL, 0.125 ug/mL, 0.083 ug/mL, and 100 ul was added into each sample. Meanwhile, the negative control (hIgG1) was set. 5 ug/ml, 0.05 ug/ml, or 0.005 ug/ml were added into all samples at the same time and 100 ul was added into each sample. The negative control (hIgG1) was also control. 5 ug hPD-1(ECD)-Fc-Biotin was added into each sample at the same time, and incubated at 4° C. for 20 min. (3) The cells were washed twice with PBS, SA-PE (eBioscien Co.) was added. After incubation at 4° C. for 20 min, the cells were washed twice with PBS, and detected with a flow cytometer (BD FACS Calibur) and Graphpad prism6 software was used for data processing.

Figure 7:
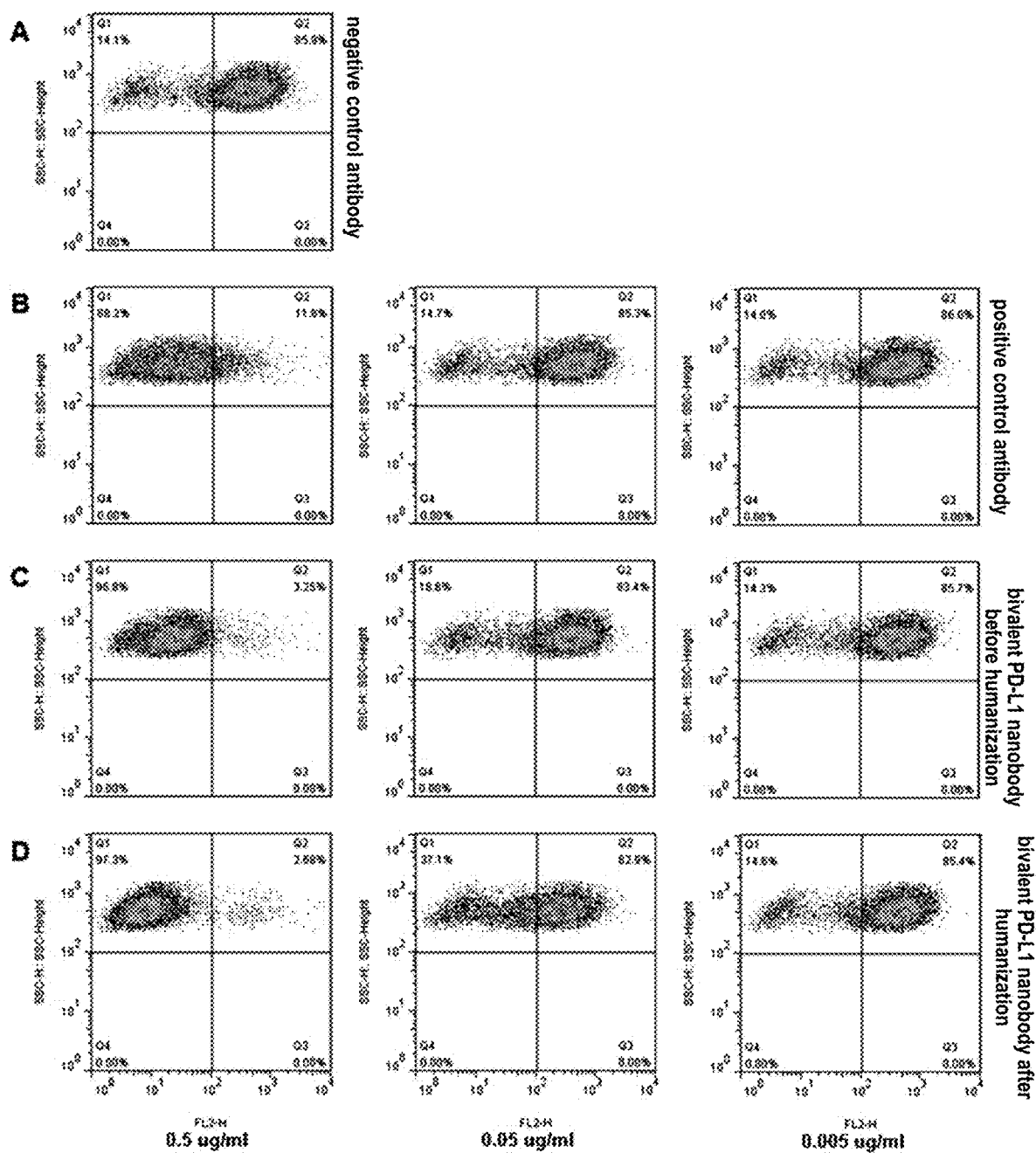
FIG. 7 shows the blocking effect of humanized bivalent anti-PD-L1 single-domain antibody fusion protein fused with FC by flow cytometry. The results showed that both bivalent anti-PD-L1 single-domain antibody before humanization and the humanized anti-PD-L1 single-domain antibody had the ability to block the interaction between PD-1 and PD-L1, and the humanized anti-PD-L1 single-domain antibody had better blocking effect.

The results are shown in FIG. 7. Both the bivalent single-domain antibody before humanization and the bivalent PD-L1 single-domain antibody after humanization had the ability to block the interaction between PD-1 and PD-L1. Moreover, the humanized bivalent PD-L1 single-domain antibody had better blocking effect.

EXAMPLE 6: DETECTION OF IC50 OF HUMANIZED TETRAVALENT PD-L1 SINGLE-DOMAIN ANTIBODY VIA FLOW CYTOMETRY (1) For each sample, $3 \times 10^5$ A375/PD-L1 stably transfected cells were taken and placed in 0.5% BSA-PBS buffer. A serial of gradient dilutions of humanized bivalent PD-L1 single-domain antibody and humanized tetravalent PD-L1 single-domain antibody and control antibody, wherein the antibody gradient dilutions were 3.33 ug/mL, 2.5 ug/mL, 1.67 ug/mL, 1.25 ug/mL, 0.83 ug/mL, 0.625 ug/mL, 0.42 ug/mL, 0.31 ug/mL, 0.21 ug/mL, 0.16 ug/mL, 0.01 ug/mL and 0.08 ug/mL, and 100 ul was added into each sample. Meanwhile, a negative control (hIgG1) and a positive control (Tecentriq) were also set. 3 μg hPD-1(ECD)-Fc-Biotin was added into each sample at the same time and incubated at 4° C. for 20 min; (2) The cells were washed twice with PBS, SA-PE (eBioscien Co.) was added. After incubation at 4° C. for 20 min, the cells were washed twice with PBS, and detected with a flow cytometer (BD FACS Calibur) and Graphpad prism6 software was used for data processing.

Figure 8:
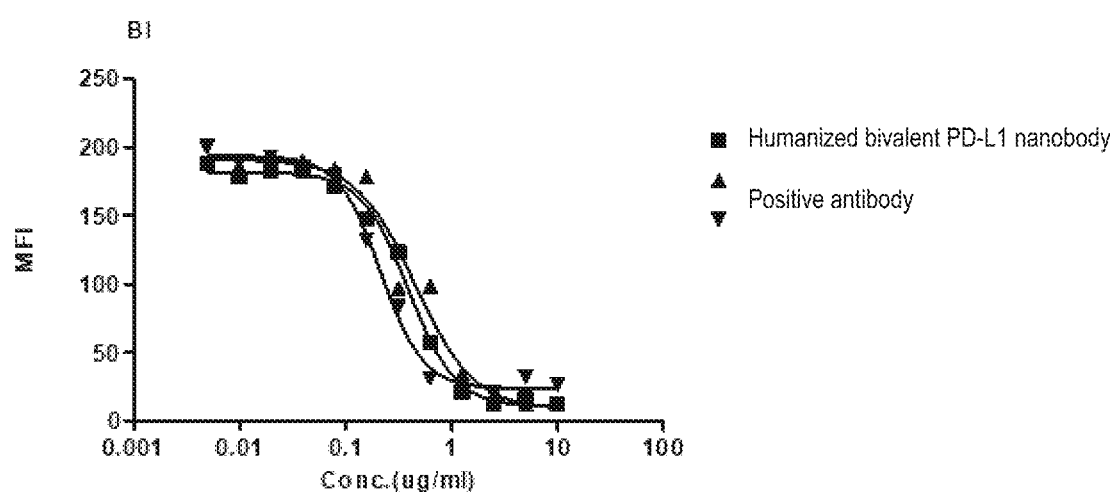
FIG. 8 shows the IC50 of the humanized bivalent anti-PD-L1 single-domain antibody and the humanized tetravalent anti-PD-L1 single-domain antibody as determined by flow cytometry. The results showed that the blocking effect of the humanized tetravalent anti-PD-L1 single-domain antibody constructed in the invention on PD-1/PD-L1 binding was better than those of the humanized bivalent anti-PD-L1 single-domain antibody and the positive antibody.

The results are shown in FIG. 8. The IC50 of the humanized bivalent PD-L1 single-domain antibody was 0.84 ug/mL, the IC50 of the positive control antibody (Tecentriq) was 0.97 ug/mL, and the IC50 of the humanized tetravalent PD-L1 single-domain antibody was 0.65 ug/mL.

EXAMPLE 7: DETECTION OF AFFINITY OF ANTIBODY VIA FORTEBIO (1) The humanized bivalent single-domain antibody and the humanized tetravalent single-domain antibody were gradient diluted from 200 nM with PBST, respectively: 200 nM, 133.3 nM, 88.9 nM, 59.3 nM, 39.5 nM, 26.3 nM. The antigen protein hPD-L1(ECD)-Fc and Fc were diluted to 40 μg/mL, respectively. (2) The operating conditions of the instrument were set as follows: temperature 30° C., shake speed 1000 rpm. The Protein A-coated probe (Fortebio Part No: 18-5010) was used to capture antibody, and capture time was 180 s; the gradient diluted antigen was bound with a binding time of 180 s; dissociation time was 300 s; 10 mM glycine (pH 1.7) was used for regeneration 3 times, 5 s for each time. (3) ForteBio's Octet System was used for on-board testing.

Figure 9:
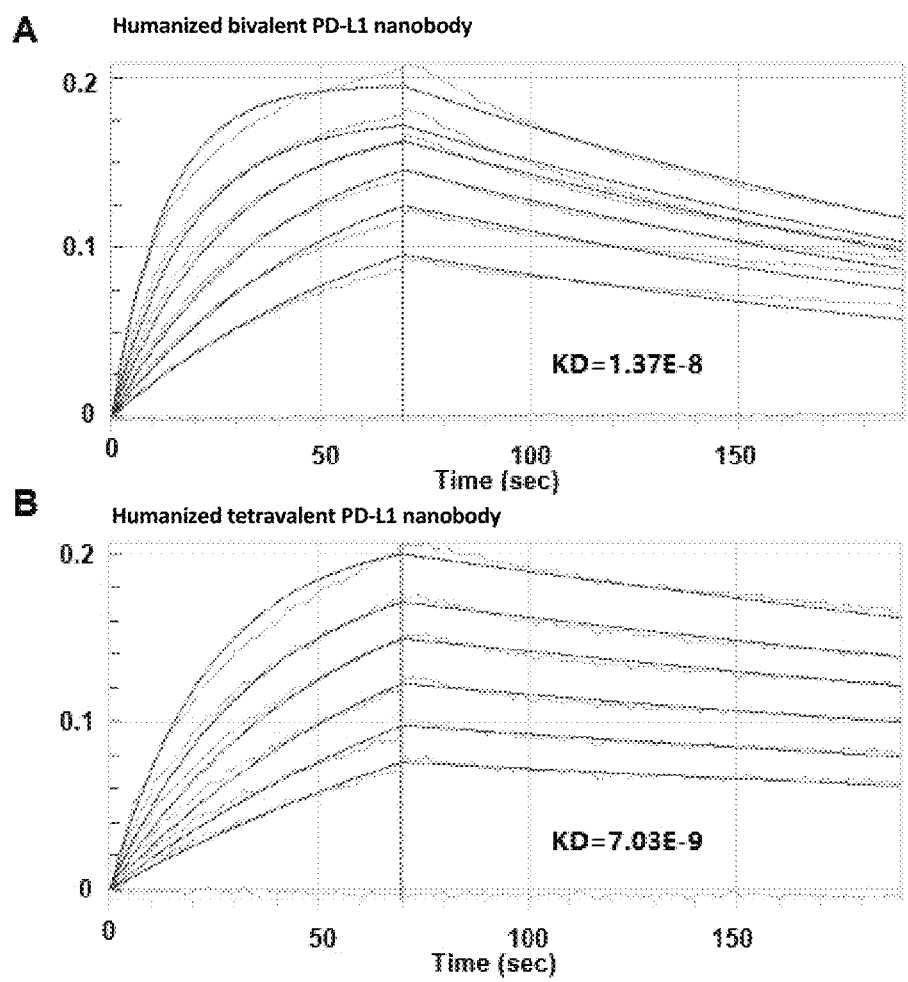
FIG. 9 shows the affinity detection results of the humanized bivalent anti-PD-L1 single-domain antibody and the humanized tetravalent anti-PD-L1 single-domain antibody. The results showed that the humanized bivalent anti-PD-L1 single-domain antibody had an affinity of 1.37e-8M, while the humanized tetravalent anti-PD-L1 single-domain antibody had an affinity of 7.03e-9M.

The test results are shown in FIG. 9: The affinity of the humanized bivalent PD-L1 single-domain antibody was 1.37E-8M, and the affinity of the humanized tetravalent PD-L1 single-domain antibody was 7.03E-9M.

EXAMPLE 8: DETECTION OF SPECIES SPECIFICITY OF PD-L1 SINGLE-DOMAIN ANTIBODY (1) The PD-L1 single-domain antibody genes before and after humanization were cloned into E. coli expression vector pMECS, and the expression and purification process was the same as in Example 4. (2) Antigen proteins PD-L1 (human), PD-L1 (rat), and PD-L1 (mouse) were coated with 0.5 μg per well (5 μg/mL, 100 μL), and IgG4 was coated as a control, and all were incubated overnight at 4° C. (3) After washing 3 times with PBST on the next day, 200 μL of 1% BSA was added to block at room temperature for 2 h. (4) After washing three times with PBST, and 100 uL of humanized single-domain antibody at a concentration of 10 μg/mL was added respectively and reacted at room temperature for 1 h. (5) The unbound antibody was washed off with PBST and mouse anti-HA antibody was added and placed at room temperature for 1 h. (6) The unbound antibody was washed off with PBST, and the goat anti-mouse alkaline phosphatase-labeled antibody was added and placed at room temperature for 1 h. (7) The unbound antibody was washed off with PBST and the alkaline phosphatase coloring solution was added and the absorbance value was read at 405 nm wavelength on an ELISA instrument.

The specificity of the single-domain antibody was determined based on the absorbance value. The detection result is shown in FIG. 10: the bivalent single-domain antibodies before and after humanization could interact with human PD-L1 and monkey PD-L1, but did not interact with murine PD-L1.

EXAMPLE 9: PURIFICATION STUDY OF HUMANIZED TETRAVALENT PD-L1 SINGLE-DOMAIN ANTIBODY AFTER ONE-STEP PURIFICATION (1) The synthesized plasmid was extracted in large quantity with a plasmid large-scale extraction kit, then mixed with PEI and transfected into HEK293F cells. The specific transfection protocol was the same as that in Example 4. (2) The protein purification protocol was also the same as that in Example 4. (3) The sample purified by one-step purification was analyzed by SEC-HPLC.

The results are shown in FIG. 11. The antibody was purified by one-step affinity purification with a purity of 99.07%, which could be used for subsequent analysis and research.

EXAMPLE 10: STABILITY STUDY OF HUMANIZED TETRAVALENT PD-L1 SINGLE-DOMAIN ANTIBODY (1) The sample of the humanized tetravalent PD-L1 single-domain antibody was concentrated or diluted to 10 mg/ml. (2) The sample was filtered into a new centrifuge tube with a 0.22 um needle filter. (3) The diluted sample storage solution (1×PBS, pH7.0) was filtered into a new centrifuge tube with a 0.22 um needle filter. (4) 10 mg/mL filtered sample was dispensed into 100 uL per tube and marked according to the corresponding name in the table below.

| Timing | Day2 | Day4 | Day6 | Day8 | Day10 |
|---|---|---|---|---|---|
| Temperature | 25° C. | 25° C. | 25° C. | 25° C. | 25° C. |

(5) The sample was configured to a final concentration of 5 mg/mL and mixed thoroughly, 100 uL per tube, dispensed and labeled according to the corresponding name in the table below for 5 mg/mL.

| Timing | Day2 | Day4 | Day6 | Day8 | Day10 |
|---|---|---|---|---|---|
| Temperature | 25° C. | 25° C. | 25° C. | 25° C. | 25° C. |

(6) The sample was configured to a final concentration of 1 mg/mL and mixed thoroughly, 100 uL per tube, dispensed and labeled according to the corresponding name in the table below;

| Timing | Day2 | Day4 | Day6 | Day8 | Day10 |
|---|---|---|---|---|---|
| Temperature | 25° C. | 25° C. | 25° C. | 25° C. | 25° C. |

(7) The sample was placed in the corresponding incubator. (8) Samples were taken and tested at the corresponding detection timing point. (9) The samples was diluted to 1 mg/ml with the mobile phase, and used as a testing sample. (10) The testing sample was centrifuged at 10,000 rpm for 3 min, and a pipette was used to transfer the sample supernatant to the sample bottle, which was put into the HPLC auto-sampler. The sample was loaded and detected.

Figure 12:
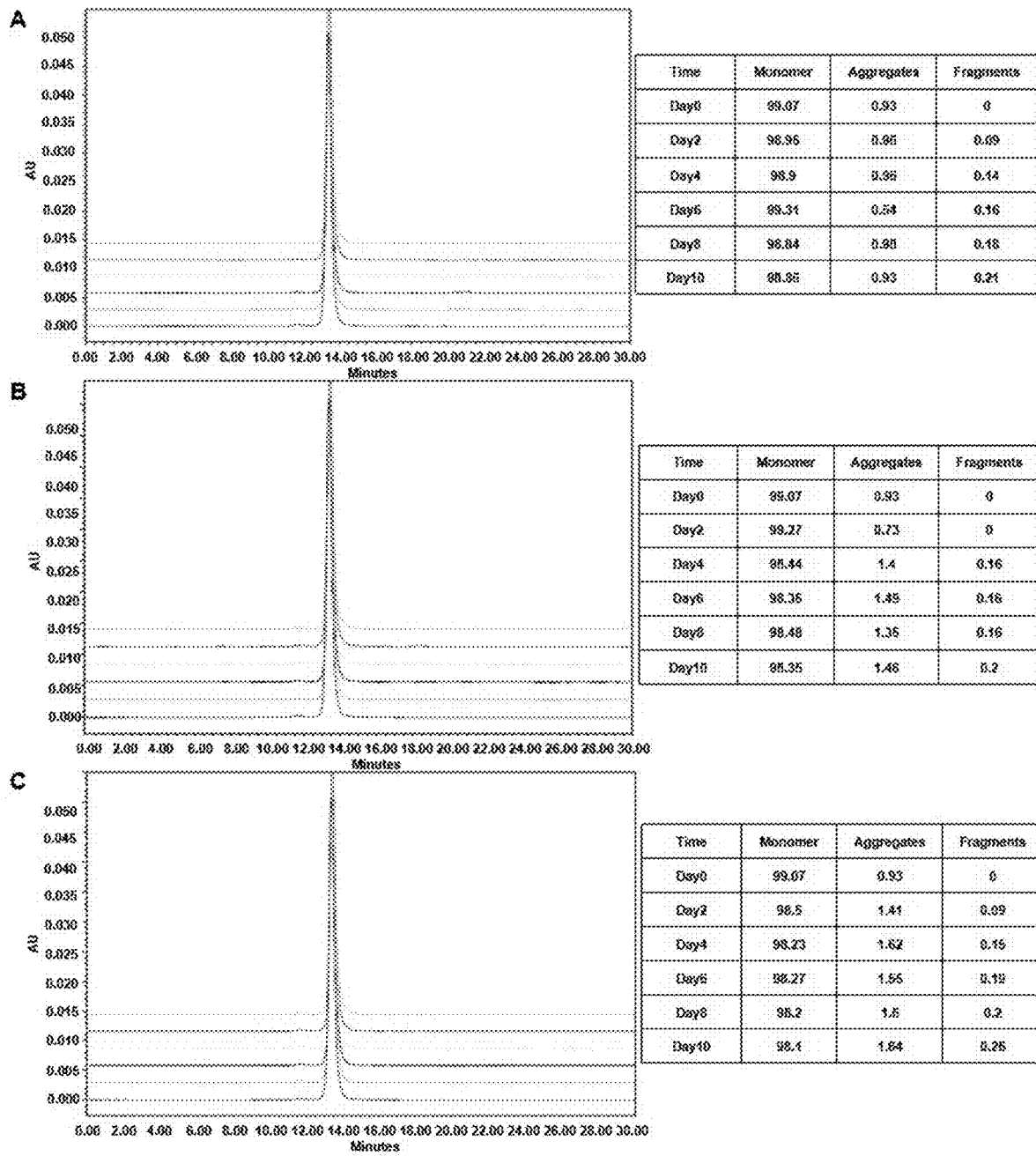
FIG. 12 shows the stability test results of the humanized tetravalent anti-PD-L1 single-domain antibody. The results showed that the antibody had no obvious aggregation or degradation at 25° C., thus exhibiting good stability.

The results are shown in FIGS. 12A-C. The antibody showed no obvious aggregation or degradation under the accelerated condition of 25° C., suggesting that the antibody had good stability.

Figure 13:
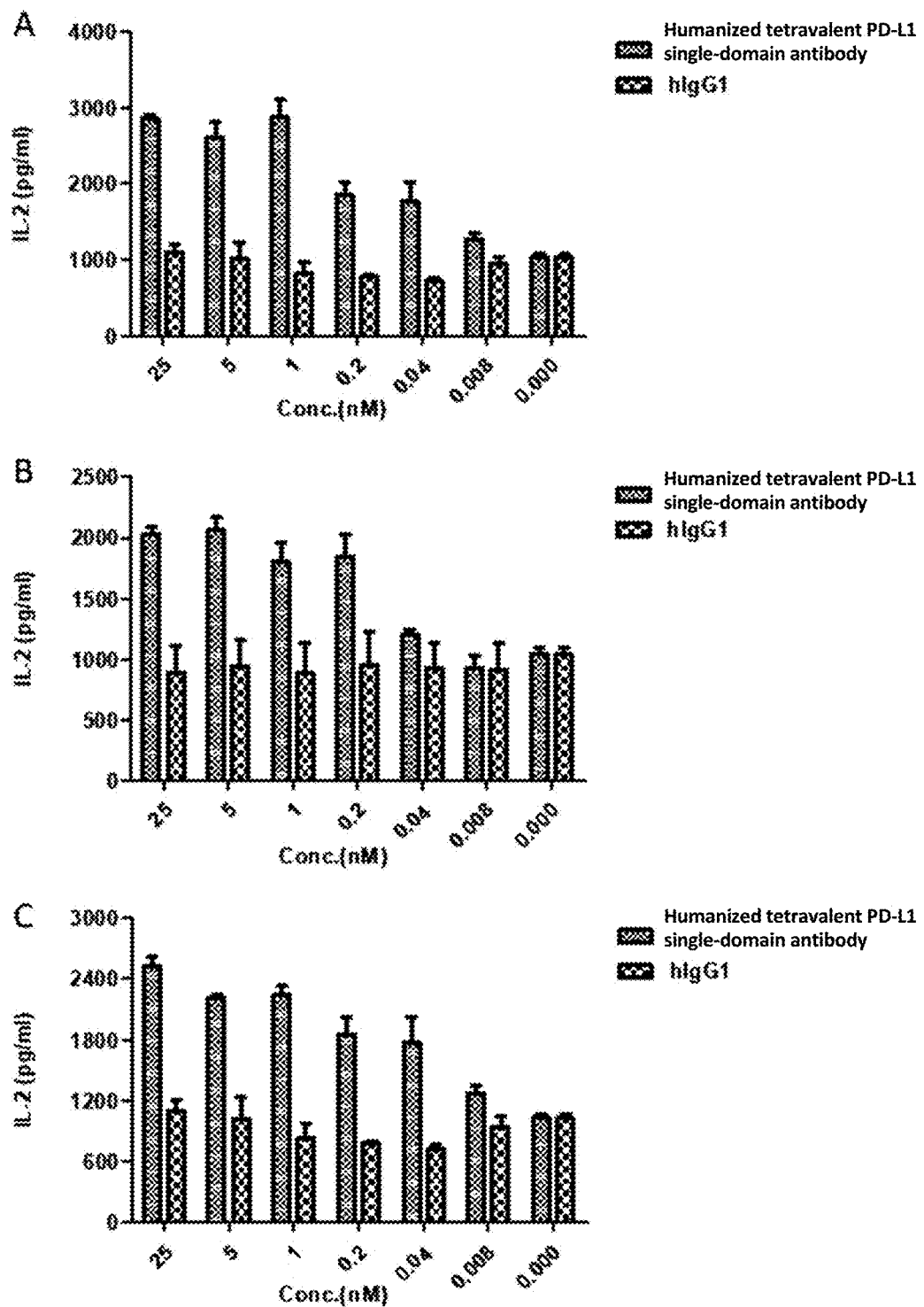
FIG. 13 shows the activation of T cells by the humanized tetravalent anti-PD-L1 single-domain antibody. The results showed that the humanized tetravalent anti-PD-L1 single-domain antibody could significantly promote T cells to release IL2.

EXAMPLE 11: T CELL ACTIVATION ACTIVITY OF HUMANIZED TETRAVALENT PD-L1 SINGLE-DOMAIN ANTIBODY (1) 3 aliquots of fresh PBMCs were taken and diluted to $2\times10^6$/ml with complete medium. (2) SEB (Toxin Technology) was diluted with complete medium to 0.4 ug/ml. The humanized tetravalent PD-L1 single-domain antibody and Tecentriq were diluted with complete medium to 50 nM, 10 nM, 2 nM, 0.4 nM, 0.08 nM, and 0.016 nM. (3) 50 ul of PBMC cells were added into the corresponding 96-well cell culture plate (Corning), respectively ($1\times10^5$/well). 50 ul of the above-prepared SEB solution and 100 ul of the antibody solution were added into the corresponding wells, and cultured at 37° C., 5% $CO_2$ for 3 days. (4) The supernatant was taken and the level of IL2 was detected by ELISA (according to the instructions of BD kit). As shown in FIGS. 13A-C, the humanized tetravalent PD-L1 single-domain antibody could significantly promote T cell to release IL2.

EXAMPLE 12: IN VIVO DRUG EFFICACY STUDY OF HUMANIZED TETRAVALENT PD-L1 SINGLE-DOMAIN ANTIBODY

Figure 14:
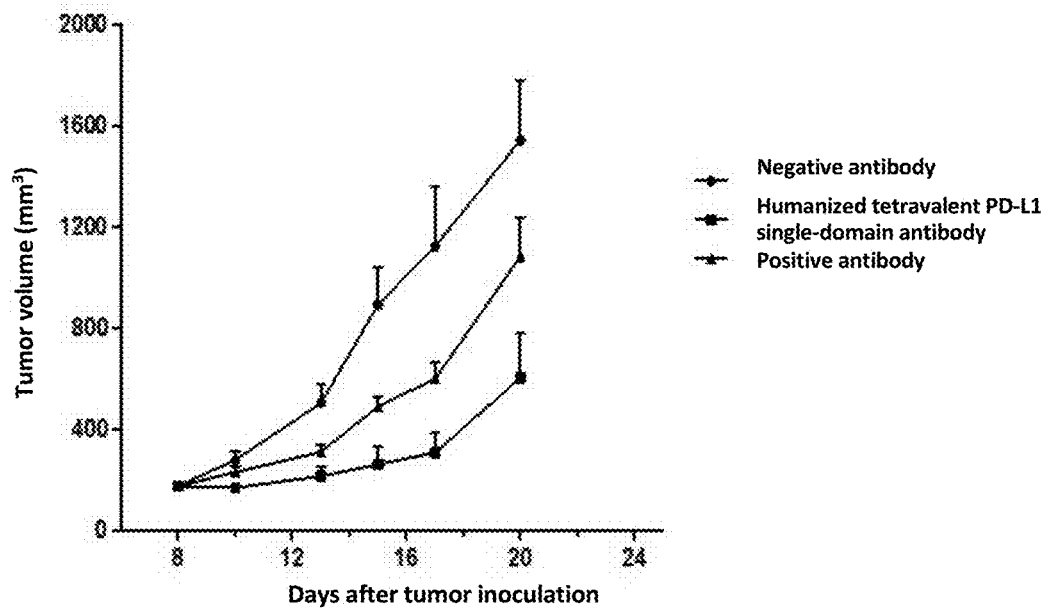
FIG. 14 shows the inhibitory effect of the humanized tetravalent anti-PD-L1 single-domain antibody on MC38 (hPD-L1) tumor in hPD-L1 transgenic mice. The results showed that the humanized tetravalent anti-PD-L1 single-domain antibody had significant tumor inhibition effect, and its 10 mpk tumor grow inhibition or TGI was 69%, which was significantly better than that of Tecentriq whose 10 mpk TGI was 34%.

The hPD-L1 transgenic mice were inoculated with MC38 (hPD-L1) cells. After tumor formation, they were divided into three groups with 8 mice in each group for administration (negative control antibody: hIgG; positive control antibody: Tecentriq; experimental group: humanized tetravalent PD-L1 single-domain antibody). Dosing frequency: twice a week, for 2 consecutive weeks. Dosage: 10 mg/kg. The results of the experiment are shown in FIG. 14: The humanized tetravalent PD-L1 single-domain antibody had a significant tumor inhibitory effect, with a tumor grow inhibition or TGI of 69%, and the tumors of two mice had completely regressed, and the tumors were in a state of complete regression during the observation period of the following three consecutive months (mice were sacrificed after 3 months). However, the tumor grow inhibition of the positive control antibody Tecentriq in this experiment was only 57%. The tumor inhibitory effect of the humanized tetravalent PD-L1 single-domain antibody was better than that of Tecentriq.

EXAMPLE 13: ANALYSIS OF CRYSTAL STRUCTURE OF ANTI-PD-L1 SINGLE-DOMAIN ANTIBODY

PD-L1 N-terminal IgV domain (amino acids 19-132) was expressed in prokaryotic cell and mixed with a refolding solution containing anti-PD-L1 single-domain antibody. The PD-L1 single-domain antibody/PD-L1 IgV complex was then purified by ion exchange. The purified PD-L1 and PD-L1/anti-PD-L1 single-domain antibody complexes were both concentrated, and the screening of crystallization were performed using a commercially available buffer and gas phase diffusion condition. PD-L1-IgV/PD-L1 single-domain antibody crystals were obtained at room temperature.

EXAMPLE 14: ANALYSIS OF PD-L1 SINGLE-DOMAIN ANTIBODY EPITOPES (1) Based on the crystal structure of PD-L1 single-domain antibody and hPD-L1, a series of point mutations were designed for hPD-L1, namely I54A, Y56A, E58A, D61A, K62A, N63A, Q66A, V68A, R113A, M115A, I116A, S117A, and Y123A.

Figure 15:
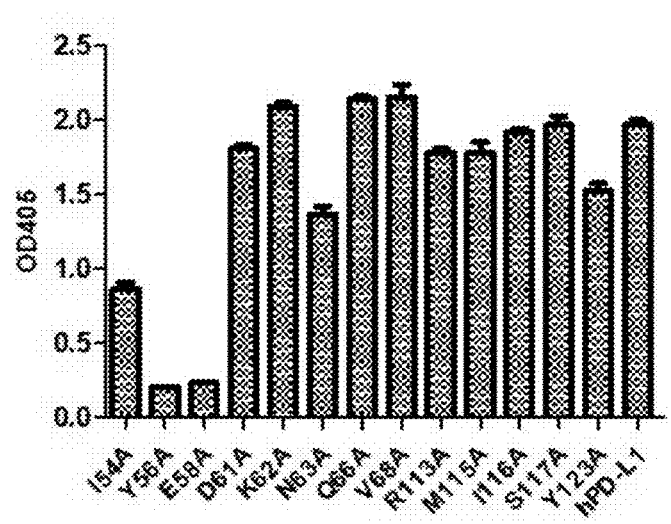
FIG. 15 shows the epitope analysis of anti-PD-L1 single-domain antibody. The results showed that the binding epitopes of anti-PD-L1 single-domain antibody were I54, Y56, E58, N63 and Y123.

(2) The binding of anti-PD-L1 single-domain antibody to different hPD-L1 with point mutation was detected via ELISA method. 100 ul PD-L1 antibody was diluted with NaHCO$_3$ solution, coated, and incubated overnight at 4° C. After washing with PBST for 5 times, 1% BSA was used for blocking at room temperature for 2 hours. PBST was used to wash for 5 times. The anti-PD-L1 single-domain antibody was diluted with PBS to obtain antibody dilution. Each well had 100 ul of sample and was incubated at room temperature for 1 h. After washing with PBST for 5 times, 100 ul anti-HA (mouse) (1:2000 PBS dilution) was added and incubated at room temperature for 1 hour. After washing with PBST for 5 times, 100 ul anti-mouse antibody (1:2000 PBS dilution) was added and placed at 37° C. for 30 min. After the incubation with secondary antibody was completed, 300 ul PBST was used to washing (5 times). 100 ul coloring solution was added into each well by using a multiple micropipette and reacted in dark and at room temperature for 10 min. The absorbance value at 405 nm was measured with a microplate reader. The results are shown in FIG. 15. The binding epitopes of the anti-PD-L1 single-domain antibody were I54, Y56, D61, E58, N63, and Y123.

All literatures mentioned in the present application are incorporated by reference herein, as if each is individually incorporated by reference. Additionally, it should be understood that after reading the above teaching, many variations and modifications may be made by the skilled in the art, and these equivalents also fall within the scope as defined by the appended claims.

The invention claimed is:

1. An anti-PD-L1 single-domain antibody, which is a single-domain antibody targeting PD-L1 epitope and has a VHH chain comprising the following 3 complementarity determining regions (CDRs) wherein CDR1 comprises SEQ ID NO: 5, CDR2 comprises SEQ ID NO: 6, and CDR3 comprises SEQ ID NO: 7.

2. The anti-PD-L1 single-domain antibody of claim 1, wherein the single-domain antibody comprises monomer, divalent, and tetravalent forms.

3. The anti-PD-L1 single-domain antibody of claim 1, wherein the VHH chain comprises 4 framework regions (FRs).

4. The anti-PD-L1 single-domain antibody of claim 3, wherein the four framework regions are selected from the group consisting of (a) FR1 comprising SEQ ID NO: 1, FR2 comprising SEQ ID NO: 2, FR3 comprising SEQ ID NO: 3, and FR4 comprising SEQ ID NO: 4; and (b) FR1 comprising SEQ ID NO: 10, FR2 comprising SEQ ID NO: 11, FR3 comprising SEQ ID NO: 12, and FR4 comprising SEQ ID NO: 13.

5. The anti-PD-L1 single-domain antibody of claim 1, wherein the single-domain antibody has a VHH chain comprising SEQ ID NO: 8 or SEQ ID NO: 14.

6. The anti-PD-L1 single-domain antibody of claim 1, which is a tetravalent anti-PD-L1 single-domain antibody, which has the following structure:

A-L-P~P-L-A;

wherein,
element P is a monomer of an anti-PD-L1 single-domain antibody whose VHH chain comprises the following 3 CDRs wherein CDR1 comprises SEQ ID NO: 5, CDR2 comprises SEQ ID NO: 6, and CDR3 comprises SEQ ID NO: 7;
element A is a sequence comprising SEQ ID NO: 14;
L represents a linker;
"_" represents a peptide bond; and
"~" represents a disulfide bond.

7. A humanized tetravalent anti-PD-L1 single-domain antibody comprising SEQ ID NO: 18.

8. An anti-PD-L1 single-domain antibody comprising SEQ ID NO: 14 fused with a human immunoglobulin IgG1 amino acid sequence, and the amino acid sequence of the PD-L1 single-domain antibody comprising SEQ ID NO: 16.

9. A polynucleotide which encodes an anti-PD-L1 single-domain antibody of claim 1.

10. An expression vector containing the polynucleotide of claim 9.

11. A host cell expressing a polynucleotide that encodes an anti-PD-L1 single-domain antibody of claim 1.

12. A conjugate prepared by linking a chemical label or a biomarker with the anti-PD-L1 single-domain antibody of claim 1.

13. A kit comprising the anti-PD-L1 single-domain antibody of claim 1 or a conjugate thereof.

14. A pharmaceutical composition which comprises the anti-PD-L1 single-domain antibody of claim 1 and one or more pharmaceutically acceptable carriers.

15. A host cell which contains the expression vector of claim 10.

* * * * *

SEQUENCE LISTING

```
<160> NUMBER OF SEQ ID NOS: 19

<210> SEQ ID NO 1
<211> LENGTH: 25
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: framework region 1

<400> SEQUENCE: 1

Gln Val Gln Leu Gln Glu Ser Gly Gly Gly Ser Val Gln Ala Gly Gly
1               5                   10                  15

Ser Leu Arg Leu Ser Cys Thr Ala Ser
            20                  25

<210> SEQ ID NO 2
<211> LENGTH: 15
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: framework region 2

<400> SEQUENCE: 2

Trp Phe Arg Gln Ala Pro Gly Lys Glu Arg Glu Gly Val Ala Phe
1               5                   10                  15

<210> SEQ ID NO 3
<211> LENGTH: 38
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: framework region 3

<400> SEQUENCE: 3
```

Arg Tyr Ala Asp Ser Val Lys Ala Arg Phe Thr Ile Ser Arg Asp Asn
1               5                   10                  15

Ala Glu Asn Thr Leu Tyr Leu Gln Met Asn Ser Leu Lys Pro Glu Asp
                20                  25                  30

Thr Ala Met Tyr Tyr Cys
            35

<210> SEQ ID NO 4
<211> LENGTH: 11
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: framework region 4

<400> SEQUENCE: 4

Arg Gly Gln Gly Thr Gln Val Thr Val Ser Ser
1               5                   10

<210> SEQ ID NO 5
<211> LENGTH: 10
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: complementarity determining region 1

<400> SEQUENCE: 5

Gly Tyr Asn Leu Ser Pro Ser Cys Met Gly
1               5                   10

<210> SEQ ID NO 6
<211> LENGTH: 7
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: complementarity determining region 2

<400> SEQUENCE: 6

Thr Asp Ala Asp Gly Ser Thr
1               5

<210> SEQ ID NO 7
<211> LENGTH: 20
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: complementarity determining region 3

<400> SEQUENCE: 7

Ala Ala Asp Phe Phe Ser Tyr Cys Ser Val Val Phe Arg Ala Ser Ala
1               5                   10                  15

Arg Asp Lys Tyr
            20

<210> SEQ ID NO 8

```
<211> LENGTH: 126
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: full length sequence

<400> SEQUENCE: 8
```

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Asn Leu Ser Pro Ser
            20                  25                  30

Cys Met Gly Trp Phe Arg Gln Ala Pro Gly Lys Glu Arg Glu Gly Val
        35                  40                  45

Ala Phe Thr Asp Ala Asp Gly Ser Thr Arg Tyr Ala Asp Ser Val Lys
    50                  55                  60

Ala Arg Phe Thr Ile Ser Arg Asp Asn Ala Glu Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Phe Phe Ser Tyr Cys Ser Val Val Phe Arg Ala Ser Ala Arg
            100                 105                 110

Asp Lys Tyr Arg Gly Gln Gly Thr Gln Val Thr Val Ser Ser
        115                 120                 125

```
<210> SEQ ID NO 9
<211> LENGTH: 378
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: full length encoding nucleotide sequence

<400> SEQUENCE: 9
caggtgcagc tgcaggagtc tgggggaggc tcggtgcagg ctggagggtc tctgagactc        60
tcctgtacag cctctggata caacttgagt cccagctgca tgggctggtt ccgccaggct       120
ccagggaagg agcgcgaggg ggtcgcattt acagatgctg atggtagcac aagatacgca       180
gactctgtga aggcccggtt caccatctcc cgagacaacg ccgagaacac tctgtatctg       240
caaatgaaca gcctgaaacc tgaggacact gccatgtact actgtgcggc agatttcttt       300
tcttactgct cggtcgtctt ccgggcgagt gcccgcgata agtaccgggg ccaggggacc       360
caggtcaccg tctcctca                                                    378

<210> SEQ ID NO 10
<211> LENGTH: 25
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: humanized framework region 1

<400> SEQUENCE: 10
```

Gln Val Gln Leu Gln Glu Ser Gly Gly Gly Leu Val Gln Pro Gly Gly
1               5                   10                  15

Ser Leu Arg Leu Ser Cys Thr Ala Ser
            20                  25

```
            20                  25

<210> SEQ ID NO 11
<211> LENGTH: 15
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: humanized framework region 2

<400> SEQUENCE: 11

Trp Phe Arg Gln Ala Pro Gly Lys Gly Leu Glu Gly Val Ala Phe
1               5                  10                  15

<210> SEQ ID NO 12
<211> LENGTH: 38
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: humanized framework region 3

<400> SEQUENCE: 12

Arg Tyr Ala Asp Ser Val Lys Ala Arg Phe Thr Ile Ser Arg Asp Asn
1               5                  10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 13
<211> LENGTH: 11
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: humanized framework region 4

<400> SEQUENCE: 13

Arg Gly Gln Gly Thr Leu Val Thr Val Ser Ser
1               5                  10

<210> SEQ ID NO 14
<211> LENGTH: 126
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: humanized full length sequence

<400> SEQUENCE: 14

Gln Val Gln Leu Gln Glu Ser Gly Gly Gly Leu Val Gln Pro Gly Gly
1               5                  10                  15

Ser Leu Arg Leu Ser Cys Thr Ala Ser Gly Tyr Asn Leu Ser Pro Ser
            20                  25                  30

Cys Met Gly Trp Phe Arg Gln Ala Pro Gly Lys Gly Leu Glu Gly Val
        35                  40                  45

Ala Phe Thr Asp Ala Asp Gly Ser Thr Arg Tyr Ala Asp Ser Val Lys
```

```
                50                  55                  60
Ala Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                    85                  90                  95

Ala Asp Phe Phe Ser Tyr Cys Ser Val Val Phe Arg Ala Ser Ala Arg
                100                 105                 110

Asp Lys Tyr Arg Gly Gln Gly Thr Leu Val Thr Val Ser Ser
            115                 120                 125
```

<210> SEQ ID NO 15
<211> LENGTH: 378
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: humanized full length encoding nucleotide sequence

<400> SEQUENCE: 15

```
caggtgcagc tgcaggagtc cggcggcggc ctggtgcagc ccggcggctc cctgaggctg      60
tcctgcaccg cctccggcta caacctgtcc cctcctgca tgggctggtt caggcaggcc     120
cccggcaagg gcctggaggg cgtggccttc accgacgccg acggctccac caggtacgcc     180
gactccgtga aggccaggtt caccatctcc agggacaact ccaagaacac cctgtacctg     240
cagatgaact ccctgagggc cgaggacacc gccgtgtact actgcgccgc cgacttcttc     300
tcctactgct ccgtggtgtt cagggcctcc gccagggaca gtacagggg ccagggcacc     360
ctggtgaccg tgtcctcc                                                   378
```

<210> SEQ ID NO 16
<211> LENGTH: 353
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: fusion protein

<400> SEQUENCE: 16

```
Gln Val Gln Leu Gln Glu Ser Gly Gly Gly Leu Val Gln Pro Gly Gly
  1               5                  10                  15

Ser Leu Arg Leu Ser Cys Thr Ala Ser Gly Tyr Asn Leu Ser Pro Ser
                 20                  25                  30

Cys Met Gly Trp Phe Arg Gln Ala Pro Gly Lys Gly Leu Glu Gly Val
             35                  40                  45

Ala Phe Thr Asp Ala Asp Gly Ser Thr Arg Tyr Ala Asp Ser Val Lys
 50                  55                  60

Ala Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                    85                  90                  95

Ala Asp Phe Phe Ser Tyr Cys Ser Val Val Phe Arg Ala Ser Ala Arg
                100                 105                 110

Asp Lys Tyr Arg Gly Gln Gly Thr Leu Val Thr Val Ser Ser Asp Lys
            115                 120                 125
```

Thr His Thr Cys Pro Pro Cys Pro Ala Pro Glu Leu Leu Gly Gly Pro
        130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Ala Ser Thr Tyr Arg Val
        195                 200                 205

Val Ser Val Leu Thr Val Leu His Gln Asp Trp Leu Asn Gly Lys Glu
210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 17
<211> LENGTH: 8
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: linker sequence

<400> SEQUENCE: 17

Gly Gly Gly Ser Gly Gly Gly Ser
1               5

<210> SEQ ID NO 18
<211> LENGTH: 487
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: tetravalent antibody

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Thr Ala Ser Gly Tyr Asn Leu Ser Pro Ser
            20                  25                  30

```
Cys Met Gly Trp Phe Arg Gln Ala Pro Gly Lys Gly Leu Glu Gly Val
         35                  40                  45

Ala Phe Thr Asp Ala Asp Gly Ser Thr Arg Tyr Ala Asp Ser Val Lys
 50                  55                  60

Ala Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ala Asp Phe Phe Ser Tyr Cys Ser Val Val Phe Arg Ala Ser Ala Arg
                100                 105                 110

Asp Lys Tyr Arg Gly Gln Gly Thr Leu Val Thr Val Ser Ser Gly Gly
            115                 120                 125

Gly Ser Gly Gly Gly Ser Gln Val Gln Leu Gln Glu Ser Gly Gly Gly
    130                 135                 140

Leu Val Gln Pro Gly Gly Ser Leu Arg Leu Ser Cys Thr Ala Ser Gly
145                 150                 155                 160

Tyr Asn Leu Ser Pro Ser Cys Met Gly Trp Phe Arg Gln Ala Pro Gly
                165                 170                 175

Lys Gly Leu Glu Gly Val Ala Phe Thr Asp Ala Asp Gly Ser Thr Arg
            180                 185                 190

Tyr Ala Asp Ser Val Lys Ala Arg Phe Thr Ile Ser Arg Asp Asn Ser
        195                 200                 205

Lys Asn Thr Leu Tyr Leu Gln Met Asn Ser Leu Arg Ala Glu Asp Thr
    210                 215                 220

Ala Val Tyr Tyr Cys Ala Ala Asp Phe Phe Ser Tyr Cys Ser Val Val
225                 230                 235                 240

Phe Arg Ala Ser Ala Arg Asp Lys Tyr Arg Gly Gln Gly Thr Leu Val
                245                 250                 255

Thr Val Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Ala Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Glu Glu Met Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Lys Leu Thr Val Asp Lys Ser Arg Trp Gln Gln Gly Asn Val Phe Ser
```

```
                450             455             460
Cys Ser Val Met His Glu Ala Leu His Asn His Tyr Thr Gln Lys Ser
465                 470                 475                 480

Leu Ser Leu Ser Pro Gly Lys
            485
```

<210> SEQ ID NO 19
<211> LENGTH: 1464
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: nucleotide sequence encoding tetravalent antibody

<400> SEQUENCE: 19

```
caggtgcagc tgcaggagtc cggcggcggc ctggtgcagc ccggcggctc cctgaggctg      60
tcctgcaccg cctccggcta caacctgtcc ccctcctgca tgggctggtt caggcaggcc     120
cccggcaagg gcctggaggg cgtggccttc accgacgccg acggctccac caggtacgcc     180
gactccgtga aggccaggtt caccatctcc agggacaact ccaagaacac cctgtacctg     240
cagatgaact ccctgagggc cgaggacacc gccgtgtact actgcgccgc cgacttcttc     300
tcctactgct ccgtggtgtt cagggcctcc gccaggtgac agtacagggg ccagggcacc     360
ctggtgaccg tgtcctccgg cggcggcggc agcggcggcg gcagccaggt gcagctgcag     420
gagtccggcg gcggcctggt gcagcccggc ggctccctga ggctgtcctg caccgcctcc     480
ggctacaacc tgtcccccct ctgcatgggc tggttcaggc aggccccggg caagggcctg     540
gagggcgtgg ccttcaccga cgccgacggc tccaccaggt acgccgactc cgtgaaggcc     600
aggttcacca tctccaggga caactccaag aacaccctgt acctgcagat gaactccctg     660
agggccgagg acaccgccgt gtactactgc gccgccgact tcttctccta ctgctccgtg     720
gtgttcaggg cctccgccag ggacaagtac aggggccagg gcaccctggt gaccgtgtcc     780
tccgacaaaa ctcacacatg cccaccgtgc ccagcacctg aactcctggg gggaccgtca     840
gtcttcctct tccccccaaa acccaaggac accctcatga tctcccggac ccctgaggtc     900
acatgcgtgg tggtggacgt gagccacgaa gaccctgagg tcaagttcaa ctggtacgtg     960
gacggcgtgg aggtgcataa tgccaagaca aagccgcggg aggagcagta cgccagcacg    1020
taccgtgtgg tcagcgtcct caccgtcctg caccaggact ggctgaatgg caaggagtac    1080
aagtgcaagg tctccaacaa agccctccca gccccatcg agaaaaccat ctccaaagcc    1140
aaagggcagc cccgagaacc acaggtgtac accctgcccc catcccggga ggagatgacc    1200
aagaaccagg tcagcctgac ctgcctggtc aaaggcttct atcccagcga catcgccgtg    1260
gagtgggaga gcaatgggca gccggagaac aactacaaga ccacgcctcc cgtgctggac    1320
tccgacggct ccttcttcct ctacagcaag ctcaccgtgg acaagagcag gtggcagcag    1380
gggaacgtct tctcatgctc cgtgatgcac gaggctctgc acaaccacta cacgcagaag    1440
agcctctccc tgtctccggg taaa                                           1464
```